US012605495B2

(12) United States Patent
Hlavinka et al.

(10) Patent No.: US 12,605,495 B2
(45) Date of Patent: Apr. 21, 2026

(54) METHOD AND SYSTEM FOR DETERMINING PLASMA PROTEIN CONTENT OF WHOLE BLOOD USING REFRACTOMETRY

(71) Applicant: Terumo BCT, Inc., Lakewood, CO (US)

(72) Inventors: Dennis J. Hlavinka, Arvada, CO (US); Thomas J. Felt, Boulder, CO (US)

(73) Assignee: Terumo BCT, Inc., Lakewood, CO (US)

( * ) Notice: Subject to any disclaimer, the term of this patent is extended or adjusted under 35 U.S.C. 154(b) by 738 days.

(21) Appl. No.: 17/963,527

(22) Filed: Oct. 11, 2022

(65) Prior Publication Data

US 2023/0129832 A1 Apr. 27, 2023

Related U.S. Application Data

(60) Provisional application No. 63/271,033, filed on Oct. 22, 2021.

(51) Int. Cl.
*A61M 1/34* (2006.01)
*G01N 21/03* (2006.01)
(Continued)

(52) U.S. Cl.
CPC ........ *A61M 1/3403* (2014.02); *A61M 1/3496* (2013.01); *G01N 21/0303* (2013.01);
(Continued)

(58) Field of Classification Search
None
See application file for complete search history.

(56) References Cited

U.S. PATENT DOCUMENTS 5,061,632 A * 10/1991 Shepherd ............. G01N 21/314
436/66
6,462,809 B1 * 10/2002 Ryan ...................... G01N 21/43
356/136
(Continued)

FOREIGN PATENT DOCUMENTS

JP 2019-536987 A 12/2019
WO 1994-003774 A1 2/1994
WO 2018-071255 A1 4/2018

OTHER PUBLICATIONS

Office Action for corresponding Japanese Patent Application No. 2024-523562 dated Feb. 25, 2025 (14 pages).
(Continued)

*Primary Examiner* — Jonathan M Peo
(74) *Attorney, Agent, or Firm* — Harness, Dickey & Pierce, P.L.C.

(57) ABSTRACT

A method and system is provided that measures plasma protein levels of whole blood while a plasma donor is connected to an apheresis machine. A refractometer associated with the apheresis machine is capable of receiving a portion of a disposable tubing set including an integrated cuvette and prism. The integrated cuvette of the disposable tubing set can be inserted into a receiving space of the refractometer associated with the apheresis machine such that the light source and the sensor are oriented relative to the prism and a sensing surface of the integrated cuvette in a precise alignment. Calibration of the refractometer is made using anticoagulant pumped through the disposable tubing set including the integrated cuvette and prism. Based on a light intensity associated with this calibration, whole blood is then measured to determine plasma protein levels and donor eligibility.

17 Claims, 22 Drawing Sheets

(51) Int. Cl.

| | | |
|---|---|---|
| *G01N 21/17* | (2006.01) | |
| *G01N 21/41* | (2006.01) | |
| *G01N 21/85* | (2006.01) | |

(52) U.S. Cl.
CPC ......... *G01N 21/4133* (2013.01); *G01N 21/85* (2013.01); *A61M 2205/3313* (2013.01); *A61M 2205/70* (2013.01); *A61M 2230/20* (2013.01); *G01N 2021/177* (2013.01)

(56) References Cited

U.S. PATENT DOCUMENTS

| | | | |
|---|---|---|---|
| 6,816,248 B2 | 11/2004 | Sharma et al. | |
| 10,168,278 B2 | 1/2019 | Schonbrun et al. | |
| 11,150,193 B2 | 10/2021 | Moriuchi et al. | |
| 2007/0109541 A1 | 5/2007 | Mato et al. | |
| 2015/0025341 A1 | 1/2015 | Sakota et al. | |
| 2018/0106720 A1* | 4/2018 | Schonbrun | G01N 33/6803 |
| 2019/0033301 A1* | 1/2019 | Bornhop | G01N 33/536 |
| 2021/0096070 A1 | 4/2021 | Vesma | |
| 2021/0100943 A1* | 4/2021 | Min | A61M 1/3672 |

OTHER PUBLICATIONS

International Search Report and Written Opinion for corresponding International Application No. PCT/US2022/047139 dated Feb. 2, 2023 (8 Pages).

Buzanovskii V A; "Determination of Proteins in Blood. Part 3: Systematization of Methods for the Determination of Protein Compounds in Blood"; Review Journal of Chemistry, Pleiades Publishing, Moscow; vol. 7, No. 3; Aug. 31, 2017; (pp. 261-333).

Rabe, Martin et al.; "Albumin Displacement at the Air-Water Interface by Tween (Polysorbate) Surfactants"; European Biophysics Journal, Springer, DE; vol. 49, No. 7; Sep. 11, 2020; (pp. 533-547).

Extended European Search Report for corresponding International Application No. PCT/U82022/047139 dated Aug. 12, 2025 (9 pgs).

International Search Report for corresponding International Patent Application No. PCT/US2025/056075 dated Feb. 3, 2025 (11 pgs).

Written Opinion for corresponding International Patent Application No. PCT/US2025/056075 dated Feb. 3, 2025 (2 pgs).

* cited by examiner

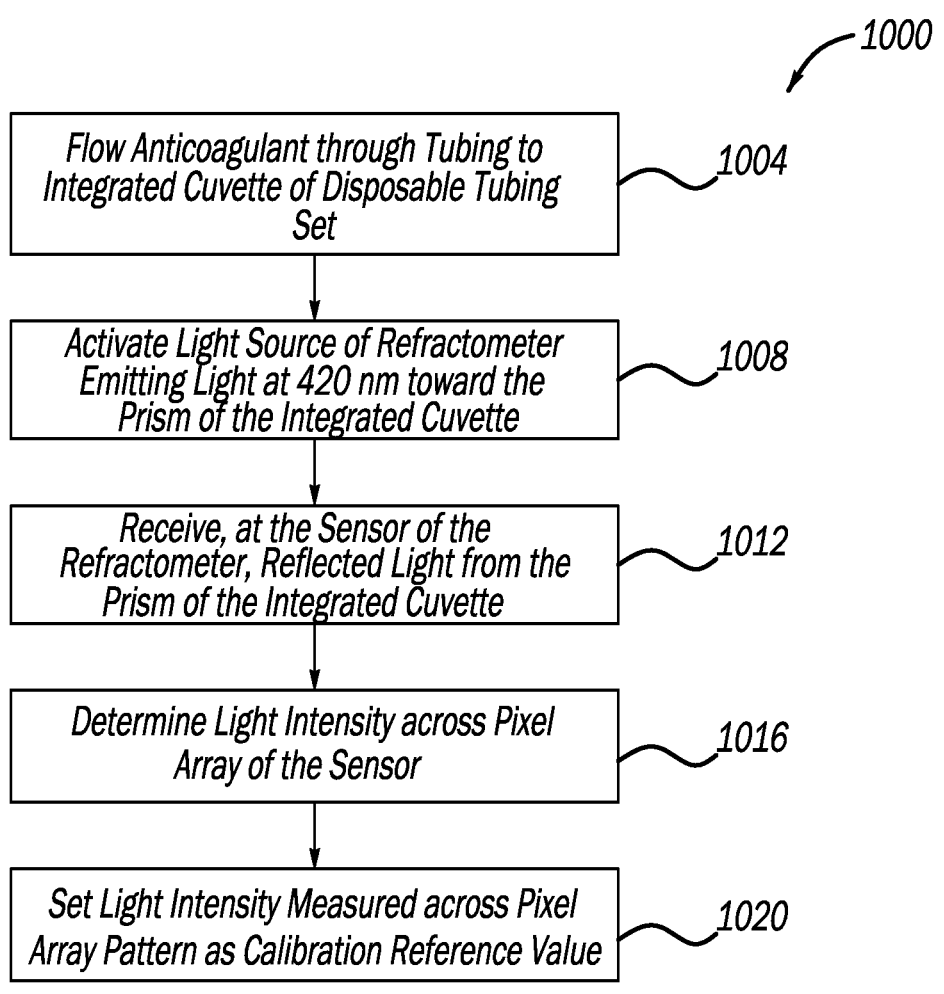

*1000*

Flow Anticoagulant through Tubing to Integrated Cuvette of Disposable Tubing Set   *1004*

Activate Light Source of Refractometer Emitting Light at 420 nm toward the Prism of the Integrated Cuvette   *1008*

Receive, at the Sensor of the Refractometer, Reflected Light from the Prism of the Integrated Cuvette   *1012*

Determine Light Intensity across Pixel Array of the Sensor   *1016*

Set Light Intensity Measured across Pixel Array Pattern as Calibration Reference Value   *1020*

*FIG. 10*

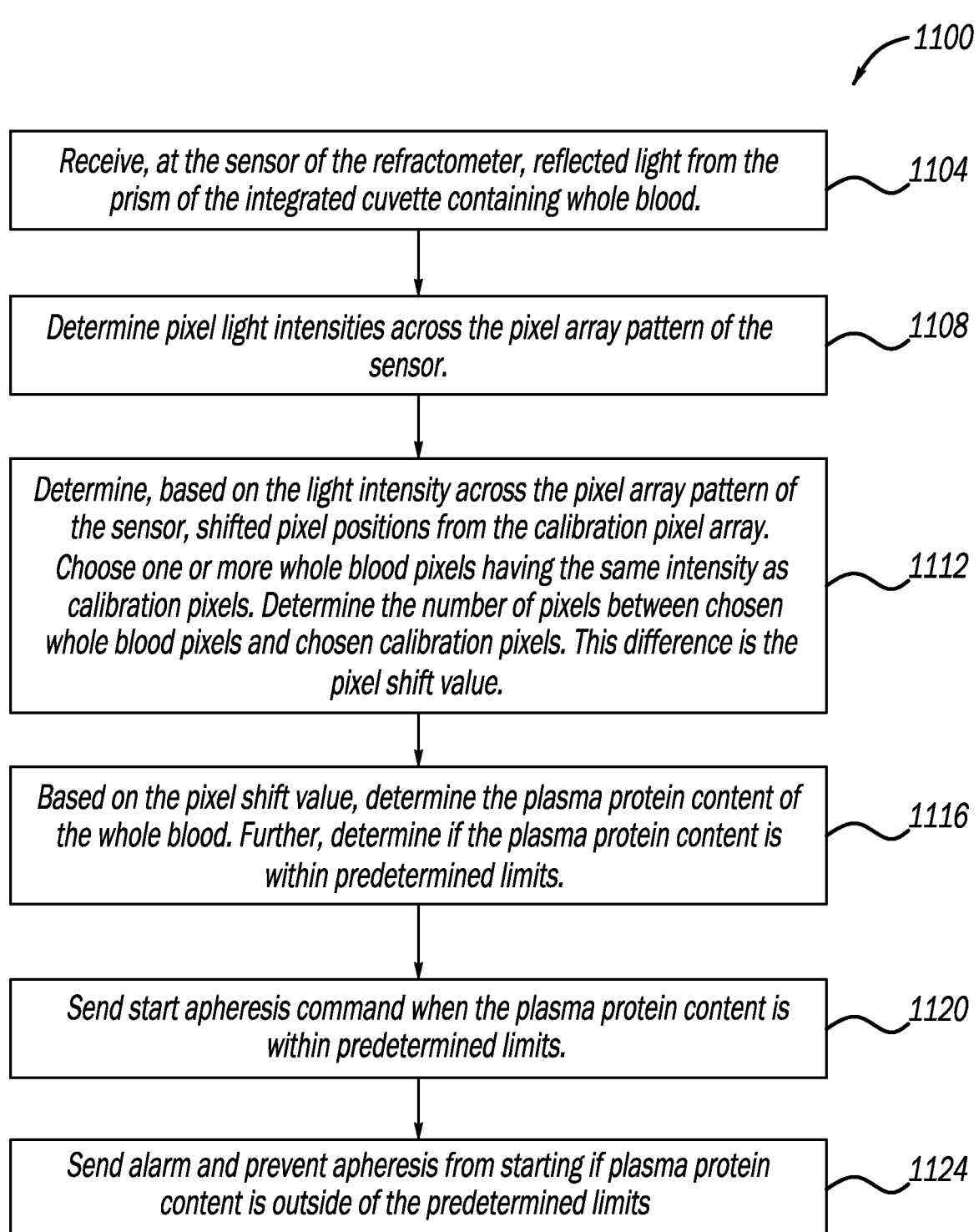

1100

Receive, at the sensor of the refractometer, reflected light from the prism of the integrated cuvette containing whole blood.    1104

Determine pixel light intensities across the pixel array pattern of the sensor.    1108

Determine, based on the light intensity across the pixel array pattern of the sensor, shifted pixel positions from the calibration pixel array. Choose one or more whole blood pixels having the same intensity as calibration pixels. Determine the number of pixels between chosen whole blood pixels and chosen calibration pixels. This difference is the pixel shift value.    1112

Based on the pixel shift value, determine the plasma protein content of the whole blood. Further, determine if the plasma protein content is within predetermined limits.    1116

Send start apheresis command when the plasma protein content is within predetermined limits.    1120

Send alarm and prevent apheresis from starting if plasma protein content is outside of the predetermined limits    1124

FIG. 11

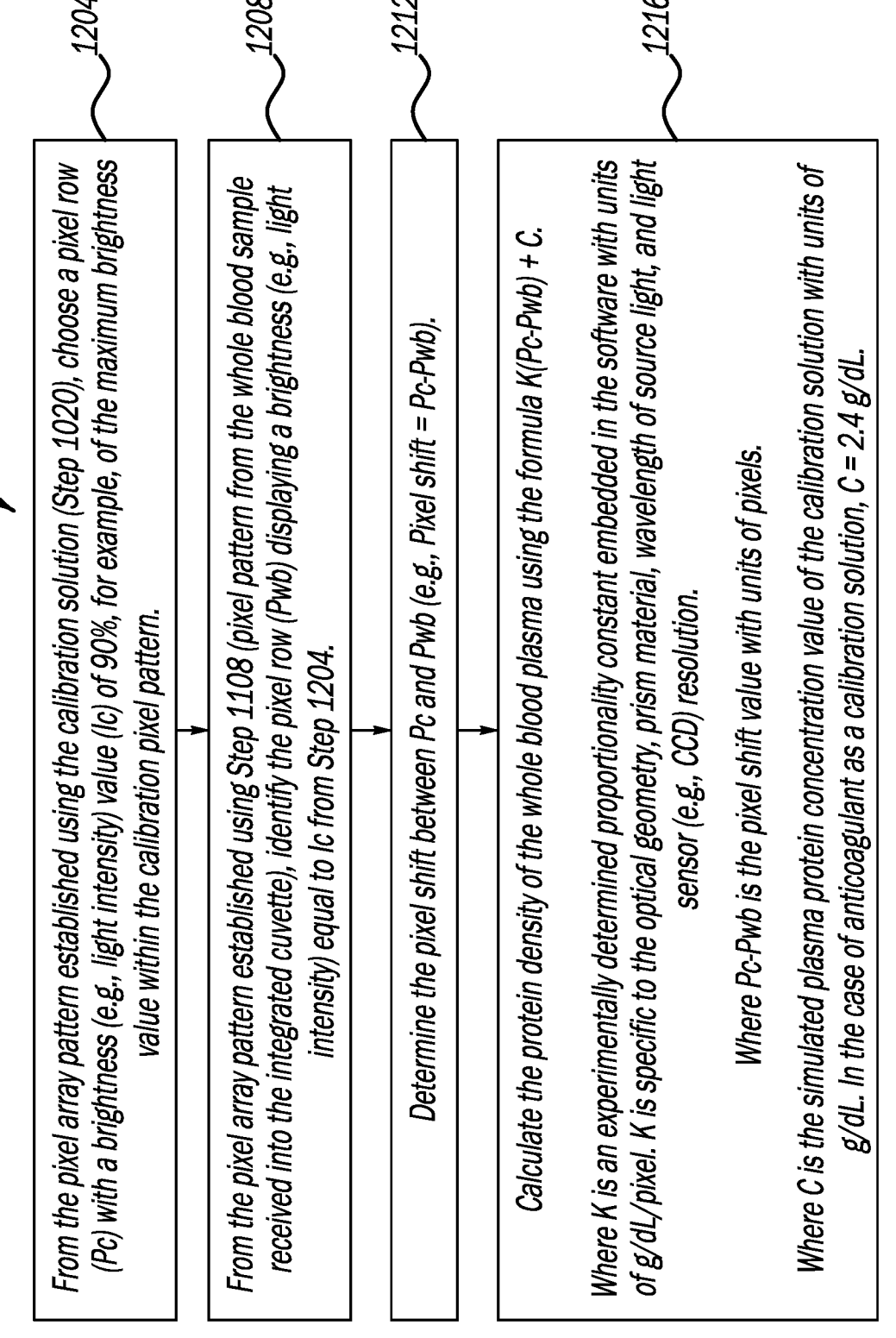

1200

1204
From the pixel array pattern established using the calibration solution (Step 1020), choose a pixel row (Pc) with a brightness (e.g., light intensity) value (Ic) of 90%, for example, of the maximum brightness value within the calibration pixel pattern.

1208
From the pixel array pattern established using Step 1108 (pixel pattern from the whole blood sample received into the integrated cuvette), identify the pixel row (Pwb) displaying a brightness (e.g., light intensity) equal to Ic from Step 1204.

1212
Determine the pixel shift between Pc and Pwb (e.g., Pixel shift = Pc-Pwb).

1216
Calculate the protein density of the whole blood plasma using the formula K(Pc-Pwb) + C.

Where K is an experimentally determined proportionality constant embedded in the software with units of g/dL/pixel. K is specific to the optical geometry, prism material, wavelength of source light, and light sensor (e.g., CCD) resolution.

Where Pc-Pwb is the pixel shift value with units of pixels.

Where C is the simulated plasma protein concentration value of the calibration solution with units of g/dL. In the case of anticoagulant as a calibration solution, C = 2.4 g/dL.

FIG. 12B

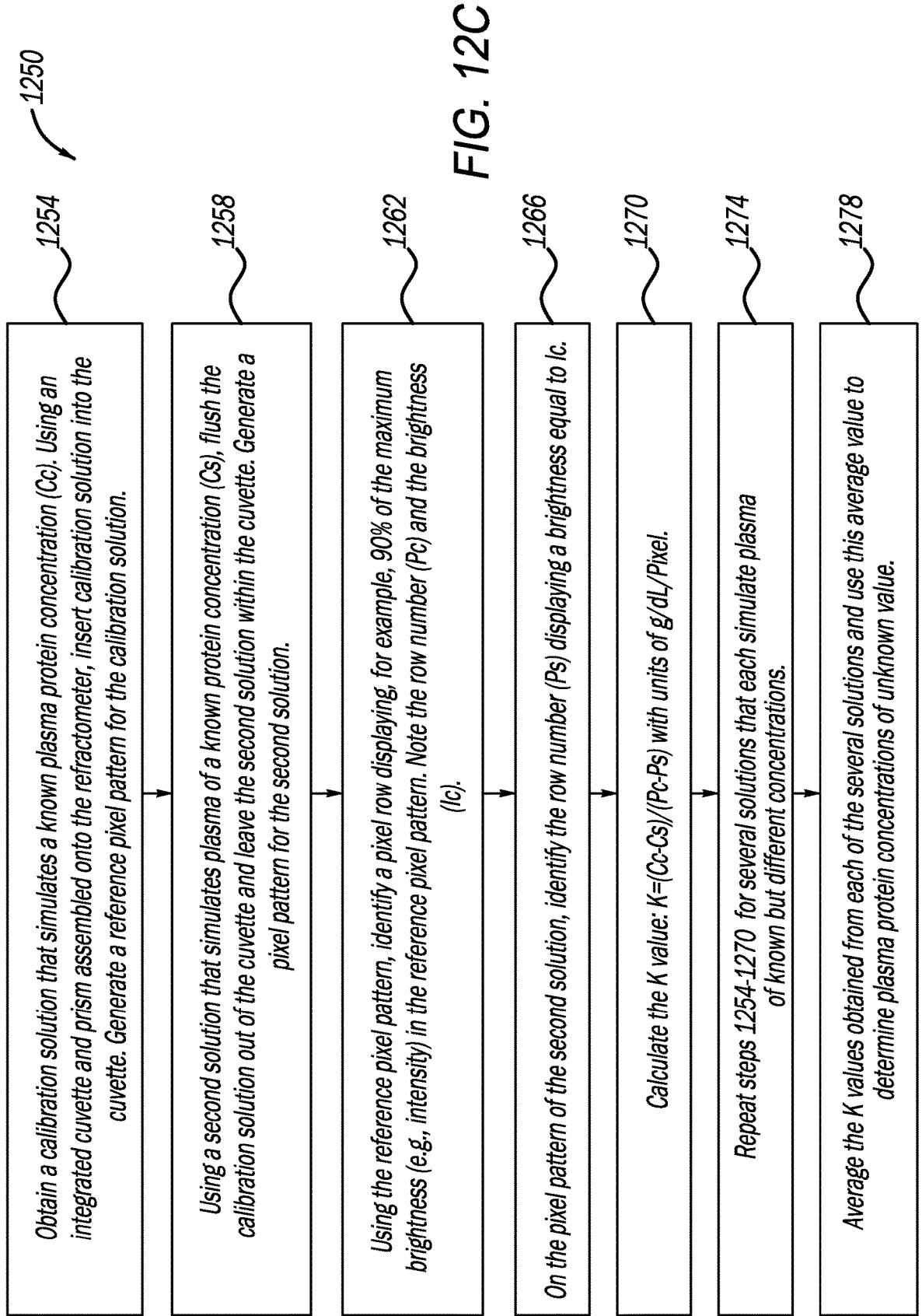

Obtain a calibration solution that simulates a known plasma protein concentration (Cc). Using an integrated cuvette and prism assembled onto the refractometer, insert calibration solution into the cuvette. Generate a reference pixel pattern for the calibration solution.

1258

Using a second solution that simulates plasma of a known protein concentration (Cs), flush the calibration solution out of the cuvette and leave the second solution within the cuvette. Generate a pixel pattern for the second solution.

1262

Using the reference pixel pattern, identify a pixel row displaying, for example, 90% of the maximum brightness (e.g., intensity) in the reference pixel pattern. Note the row number (Pc) and the brightness (Ic).

1266

On the pixel pattern of the second solution, identify the row number (Ps) displaying a brightness equal to Ic.

1270

Calculate the K value: K=(Cc-Cs)/(Pc-Ps) with units of g/dL/Pixel.

1274

Repeat steps 1254-1270 for several solutions that each simulate plasma of known but different concentrations.

1278

Average the K values obtained from each of the several solutions and use this average value to determine plasma protein concentrations of unknown value.

METHOD AND SYSTEM FOR DETERMINING PLASMA PROTEIN CONTENT OF WHOLE BLOOD USING REFRACTOMETRY

CROSS-REFERENCE TO RELATED APPLICATION

This application claims the benefit of U.S. Provisional Application No. 63/271,033 filed on Oct. 22, 2021, the entire disclosure of which is incorporated herein by reference.

BACKGROUND

The present disclosure is generally directed to refractometry, in particular, toward methods and systems for determining plasma protein content in whole blood during apheresis.

Apheresis is a method that extracts whole blood from a donor while the donor is connected to a specialized machine. The extracted whole blood may be directed through various tubing channels to a separator of the machine where the whole blood can be separated into one or more components, or constituents, of the whole blood. These components may include plasma, red blood cells, white blood cells, and platelets. During apheresis, the plasma (and/or any other desired blood component) is separated from the other blood components in the whole blood and is then collected in a bag, or bottle (e.g., for later therapeutic use, treatment, transfusion, and/or the like). The other blood components can then be returned to the donor during the apheresis process. The donor is connected to the apheresis machine during the separation and collection of the one or more blood components.

According to the United States Food and Drug Administration (FDA) a plasma donor is required to have a plasma protein level that is no less than 6.0 g/dL and no more than 9.0 g/dL to be eligible to donate plasma. See, e.g., 21 C.F.R. § 630.15 (b) (4). Currently, measuring the plasma protein level of a potential plasma donor includes collecting a blood sample by subjecting the potential plasma donor to a painful finger prick, causing the blood from the finger prick to enter a capillary tube, centrifuging the capillary tube and blood, and then placing a drop of the plasma from the capillary tube onto a handheld refractometer. The refractometer can evaluate the sample and determine the associated plasma protein level. If the plasma protein level of the sample is within the acceptable limits (e.g., 6.0 g/dL to 9.0 g/dL), the potential plasma donor is allowed to donate plasma. However, if the plasma protein level of the sample is outside of the acceptable limits (e.g., lower than 6.0 g/dL or higher than 9.0 g/dL), the potential plasma donor is not allowed to donate plasma.

BRIEF SUMMARY

It is estimated that fewer than about 1.5% of potential plasma donors are ineligible to donate their plasma due to an insufficient plasma protein level measurements. However, every donor is required to have their plasma protein levels tested to be considered eligible for donation. This results in all of the eventual plasma donors being subjected to the painful finger prick prior to donating their plasma. Among other things, the finger prick causes residual pain at the site of the finger prick, which is usually on the sensitive pad of one or more fingers, for hours, days, or longer. The teachings of the present disclosure advantageously eliminate the need for the finger prick. Moreover, the conventional process of performing this manual operation (e.g., obtaining the sample, centrifuging the sample, placing the sample into a handheld refractometer, etc.) is time consuming, complex, subject to error, and is an undesirable open blood event that requires use of personal protection equipment (PPE) and poses a potential risk to the operator.

It is with respect to the above issues and other problems that the embodiments presented herein were contemplated. The present disclosure provides a method and system for measuring plasma protein levels while the donor or patient is connected (e.g., via a needle or cannula and tubing set, etc.), to an apheresis machine, or other extracorporeal blood processing machine. In one example, the system may include a refractometer that is associated with the apheresis machine and that is capable of receiving a portion of a disposable tubing set including an integrated cuvette and prism. The integrated cuvette of the disposable tubing set can be inserted into a receiving space of the refractometer associated with the apheresis machine such that the light source (e.g., light emitting diode (LED), laser, etc.) and the sensor (e.g., charge-coupled device (CCD), complementary metal oxide semiconductor (CMOS), imaging sensor, etc.) are oriented relative to the prism and a sensing surface of the integrated cuvette in a precise alignment. For instance, the integrated cuvette and prism may include one or more kinematic features (e.g., grooves, conical recesses, chamfered slots, domed surfaces, pins, etc.) that interface with mating kinematic features disposed in the receiving space of the refractometer. Among other things, this kinematic connection (e.g., pin-in-slot, ball-in-cone, ball-and-pin, ball-and-chamfered slot connection, etc., and/or combinations thereof) may provide a reliable and accurate interconnection between an integrated cuvette and the receiving space of the refractometer. In some examples, the integrated cuvette and/or the receiving space of the refractometer may include poka-yoke features that are capable of preventing misloading of the cuvette in the receiving space of the refractometer.

The method and system of the present disclosure allows measurement of the plasma protein levels of the blood of the plasma donor to be made inline, on the apheresis machine, or other extracorporeal blood processing machine. For example, the disposable tubing set includes the integrated cuvette and prism that are used by the refractometer associated with the apheresis machine to measure plasma protein levels. The method may begin when a disposable tubing set is interconnected with the apheresis machine. At this point, the integrated cuvette and prism are engaged in the receiving space of the refractometer. Once engaged, an optical path is established that carries source light into the prism and onto the sensing surface. The sensing surface then permits passage of a portion of the light (this portion is termed refracted light) into whole blood within the cuvette. The sensing surface reflects the remaining portion of the light back into the prism and onto the external sensing system. In some examples, the prism may have a first portion disposed adjacent the light source (e.g., the LED) and a second portion disposed adjacent the sensor (e.g., the CCD), that is spaced apart from the light source. Next, the refractometer may be calibrated to the disposable tubing set including the integrated cuvette and prism. During calibration, an anticoagulant (or other suitable solution such as saline, for example) may be caused to flow through the tubing of the disposable tubing set along a fluid path to a sensing space of the integrated cuvette that is adjacent the sensing surface. While the anticoagulant is disposed in the sensing space, light emitted by the light source (e.g., the LED) may pass through the prism and onto the sensing surface of the integrated cuvette containing the anticoagulant in the sensing space. As the light interacts with the anticoagulant in the sensing space, a portion of the light may be reflected through the prism onto the sensor (e.g., the CCD). This reflected light creates a sensor reference signal which serves to establish a baseline, or reference pixel intensity pattern, for the refractometer to later perform measurements of other blood components. In one example, the anticoagulant may correspond to sodium citrate (trisodium 2-hydroxypropane-1,2,3-tricarboxylate) and water. Next, when a plasma donor is connected, for example, via a needle, catheter or cannula, to the disposable tubing set, whole blood flows along a fluid path to the sensing space of the integrated cuvette. Light emitted by the light source of the refractometer may pass through the prism and onto the sensing surface of the integrated cuvette containing the whole blood. When source light is reflected from the sensing surface, the CCD senses a modified (as compared to the anticoagulant) pixel intensity pattern. The modified pattern can be compared (as described later) to the anticoagulant pixel pattern and the protein density of the whole blood can be determined.

Although described herein as including a prism the integrated cuvette may include, without limitation, a lens, a lens stack, and/or some other optical element capable of transmitting light through at least a portion thereof. In some examples, the prism may correspond to a lens and/or include a prismatic optical element and at least one lens. As can be appreciated, the prism may be replaced by any optical shape that invokes refraction/reflection of light.

In some examples, the light emitted by the light source (e.g., the LED) may be set to a wavelength that negates interference, or noise, caused by one or more components in the whole blood. For instance, the light source may be configured to emit light at approximately 420 nm, plus or minus 50 nm, to allow refracted light encountering red blood cells to be absorbed by the red blood cells in the whole blood (e.g., rather than reflected by the red blood cells). Among other things, this select wavelength of light may allow the refractometer to measure the proteins in the plasma even if red blood cells are in the background. By removing the contribution of the red blood cells reflecting light and potentially causing signal noise, the refractometer emitting light at 420 nm can detect reflected light from the prism sensing surface, absent the first refracted light portion (which may be reflected off the RBCs and back onto the CCD sensor), to determine the protein levels in the whole blood.

In any event, when the protein level measurement falls within acceptable levels (e.g., 6.0 g/dL to 9.0 g/dL), the method may proceed by continuing apheresis. However, in the event that the protein level measurement falls outside of the acceptable levels (e.g., lower than 6.0 g/dL or higher than 9.0 g/dL), an alarm may be caused to output (e.g., audible, visual, etc., and/or combinations thereof) and the apheresis procedure may be ceased, or even prevented from beginning. In this case, the potential plasma donor would be ineligible to donate plasma and the disposable tubing set including the integrated cuvette and prism would be disposed of or otherwise discarded prior collecting plasma from the ineligible donor.

The methods and systems described herein may determine protein levels or other blood characteristics, via refractometry, prior to performing an apheresis procedure and/or during an apheresis procedure. In one example, the refractometer may determine shifts in protein levels over time for the plasma donor (e.g., during an apheresis procedure).

These shifts may cause an alarm that ceases or suspends apheresis, for example, when the protein levels dip below an acceptable threshold value. This acceptable threshold value may correspond to the acceptable lower limit of protein in whole blood (e.g., 6.0 g/dL).

It is an aspect of the present disclosure that the integrated cuvette and prism may be part of the disposable tubing set and be, in fact, disposable. Since refractometry depends on a pure optical path, or intimate contact between an optical sensing surface and light emitted therethrough, separating the cuvette from the prism or the sensing surface may cause a gap to exist between the cuvette and the light source and/or the sensor. Even a small gap of air (e.g., less than 1 micron, etc.) disposed between the prism and the sensing surface can cause refractive interference that may be unreliable for refractometric measurements of plasma protein. At least one benefit to including the prism in the cuvette of the disposable tubing set allows this gap to be removed and consistency in measurements to be maintained between disposable tubing sets.

The inline measurements performed by the refractometer and the disposable integrated cuvette described herein obviate the need for conventional time consuming and complex offline multi-step measurements of blood samples. As can be appreciated, at least one benefit of the method and system disclosed herein includes faster processing of plasma donors, for example, by allowing protein measurements to be made when a plasma donor is connected to an apheresis machine (without offline, or outside of the apheresis machine, processes or steps). As soon as the protein measurements are made by the refractometer and are determined to be within the acceptable limits, the apheresis process may start on the same apheresis machine using the same disposable tubing set. In this case, the whole blood extracted from the plasma donor may continue to pass through the integrated cuvette, which may be configured to receive flow of whole blood at a rate of up to at least 200 mL/min. The flow rate may be less than 200 mL/min and may include any flow rate value between and including 1.0 mL/min to 200 mL/min.

Moreover, the methods and systems described herein prevent the need to subject all of the plasma donors to painful finger pricks prior to donation. In any event, the disposable tubing set including the integrated cuvette and prism may be disposed of after use. This use may correspond to disposing of the disposable tubing set after the plasma protein levels have been measured and determined to be outside of the acceptable limits for a plasma donor (e.g., lower than 6.0 g/dL or higher than 9.0 g/dL). Additionally or alternatively, this use may correspond to disposing of the disposable tubing set after the plasma protein levels have been measured and determined to be within the acceptable limits for a plasma donor (e.g., at least 6.0 g/dL and no higher than 9.0 g/dL) and the apheresis process is completed using the disposable tubing set. Among other things, the ability to measure plasma protein levels for a plasma donor and either continue with apheresis (when the plasma levels are determined to be within the acceptable limits) or terminate further processing (when the plasma levels are determined to be outside of the acceptable limits), without changing the setup, provides a simple and efficient donation process.

It should be appreciated that the methods and systems disclosed herein are not limited to plasma donation or blood component separation and may be used in therapeutic apheresis, blood treatment procedures, and/or the like. Moreover, the methods and systems disclosed herein may be used by any extracorporeal blood procedures including, but in no way limited to, hemodialysis, hemodiafiltration (HDF), extracorporeal membrane oxygenation (ECMO), and/or the like. As such, the methods and systems may be used by any extracorporeal blood processing machine including, but in no way limited to, an apheresis machine or system.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages are described herein and will be apparent to those skilled in the art upon consideration of the following Detailed Description and in view of the figures.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 10 is a flow diagram of a method for calibrating a refractometer associated with an apheresis machine in accordance with embodiments of the present disclosure;

FIG. 11 is a flow diagram of a method for determining a protein level of a plasma donor while the plasma donor is connected to an apheresis machine in accordance with embodiments of the present disclosure;

FIG. 12B is a flow diagram of a method for calculating pixel shift in accordance with embodiments of the present disclosure;

FIG. 12C is a flow diagram of a method for calculating a proportionality constant K in accordance with embodiments of the present disclosure;

DETAILED DESCRIPTION

Figure 1:
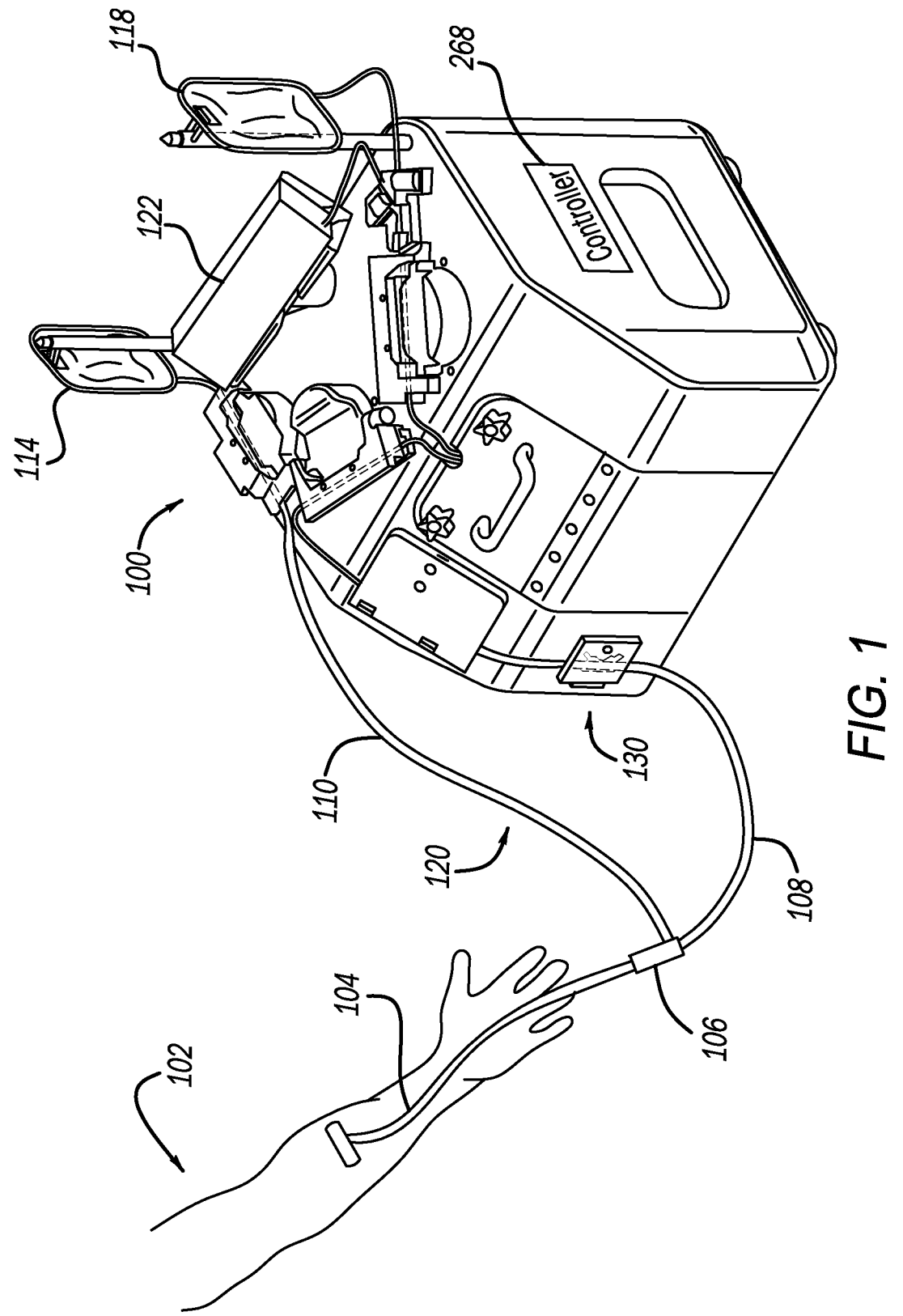
FIG. 1 shows a perspective view of an operating environment of an apheresis system and disposable tubing set including an integrated cuvette and prism in accordance with embodiments of the present disclosure.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including." "comprising." or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example." "by way of example," "e.g.," "such as," or similar language) is not intended to and does not limit the scope of the present disclosure.

The ensuing description provides embodiments only, and is not intended to limit the scope, applicability, or configuration of the claims. Rather, the ensuing description will provide those skilled in the art with an enabling description for implementing the described embodiments. It being understood that various changes may be made in the function and arrangement of elements without departing from the spirit and scope of the appended claims.

Various aspects of the present disclosure will be described herein with reference to drawings that may be schematic illustrations of idealized configurations.

Referring now to FIG. 1, a perspective view of an operating environment of an apheresis system 100 (e.g., an extracorporeal blood processing machine) and a disposable tubing set 120 including an integrated cuvette and prism is shown in accordance with embodiments of the present disclosure. The operating environment may include an apheresis system 100, a donor 102, and one or more connections (e.g., donor feed tubing 104, inlet tubing 108, anticoagulant tubing 110, etc.) running from the donor 102 to the apheresis system 100, and/or vice versa. The terms "donor," "plasma donor," and variations thereof may be used interchangeably herein. As shown in FIG. 1, donor feed tubing 104 may be fluidly connected with at least one blood vessel, for example, a vein, of a donor 102 via venipuncture. For example, a catheter, cannula, or needle, connected to an end of the donor feed tubing 104 may be inserted through the skin of the donor 102 and into a target site, or vein. This connection may provide an intravenous path for blood (e.g., whole blood) to flow from the donor 102 to the apheresis system 100, and/or for blood components to flow back to the donor 102. In some embodiments, the fluid paths and connections may form an extracorporeal tubing circuit of a disposable tubing set of the apheresis system 100.

Blood supplied from the donor 102 may flow along the donor feed tubing 104 through a tubing connector 106 and along the inlet tubing 108 into an integrated cuvette of the disposable tubing set 120. The integrated cuvette may be engaged with a receiving space 130 of a refractometer that is associated with the apheresis system 100. In some examples, the receiving space 130 may include a lid or door that covers an area housing the refractometer. The disposable tubing set may include one or more fluid control paths and valves for selectively controlling the flow of blood to and/or from the donor 102. The apheresis system 100 may include an anticoagulant supply contained in an anticoagulant bag 114. The anticoagulant may be pumped at least through anticoagulant tubing 110 and the tubing connector 106 preventing the coagulation of blood in the disposable tubing set 120 and the apheresis system 100. Although described as being contained in a bag, it should be appreciated that the anticoagulant may be stored in a bottle, a reservoir, a well, or any other container.

Anticoagulants can include one or more of, but are not limited to, citrate and/or unfractionated heparin, so long as the chemical composition remains unchanged from one apheresis procedure to next. With unchanging chemical composition, the calibration anticoagulant fluid will always simulate the same level of plasma protein concentration. For example, the anticoagulant cited in this disclosure will always simulate a plasma protein content of 2.4 gm/dL so long as the chemical composition remains unchanged. The anticoagulant bag and other bags or bottles described herein can be made from, for example, one or more of, but not limited to: polyvinyl chloride (PVC), plasticized-PVC, polyethylene, ethylene with vinyl acetate (EVA), rubber, silicone, thermoplastics, thermoplastic elastomer, polymers, copolymers, and/or combinations thereof. The volume of anticoagulant in the anticoagulant bag 114 may vary based on the various factors, including the mass of the donor 102, the volumetric flow of blood from the donor 102, etc. In one example, the volume in the anticoagulant bag 114 may be 250 to 500 mL, although the volume in the anticoagulant bag 114 may be more or less than this volume.

In some embodiments, the apheresis system 100 may include a plasma collection bottle 122, or container, a saline fluid contained in a saline bag 118, and one or more lines or tubes 116, 120 (e.g., fluid conveying tubing, etc.) connecting the saline bag 118 and the plasma collection bottle 122 with the disposable tubing set 120 of the apheresis system 100. The amount of saline provided in the saline bag 118 can be 500 to 800 mL, although the volume in the saline bag 118 may be more or less than this volume. An example donation of a blood component, e.g., plasma, may be 880 mL. Thus, the plasma collection bottle 122 may hold at least this amount of plasma. In some embodiments, the plasma collection bottle 122 may include a connection point disposed at, adjacent to, or in physical proximity to, a substantially bottommost portion of the plasma collection bottle 122 (e.g., when the plasma collection bottle 122 is installed in a plasma collection cradle). The connection point may include one or more connectors that are configured to interconnect with the plasma tubing to receive and/or convey plasma. The disposition of the connection point at the bottom of the plasma collection bottle 122 can allow plasma contained in the plasma collection bottle 122 to move out of the plasma tubing back through the lines, as described herein, without trapping air bubbles, etc. In some embodiments, the plasma collection bottle 122 may be configured as a flexible bag, rigid container, and/or other container, and thus, the plasma collection bottle 122 is not limited to bottles or bottle-like containers.

Examples of apheresis, plasmapheresis, and other separation systems that may be used with embodiments of the present disclosure, e.g., as apheresis system 100, include, but are not limited to, the RIKA plasma donation system, the SPECTRA OPTIA® apheresis system, COBE® spectra apheresis system, and the TRIMA ACCEL® automated blood collection system, all manufactured by Terumo BCT, of Lakewood, Colorado.

Figure 2A:
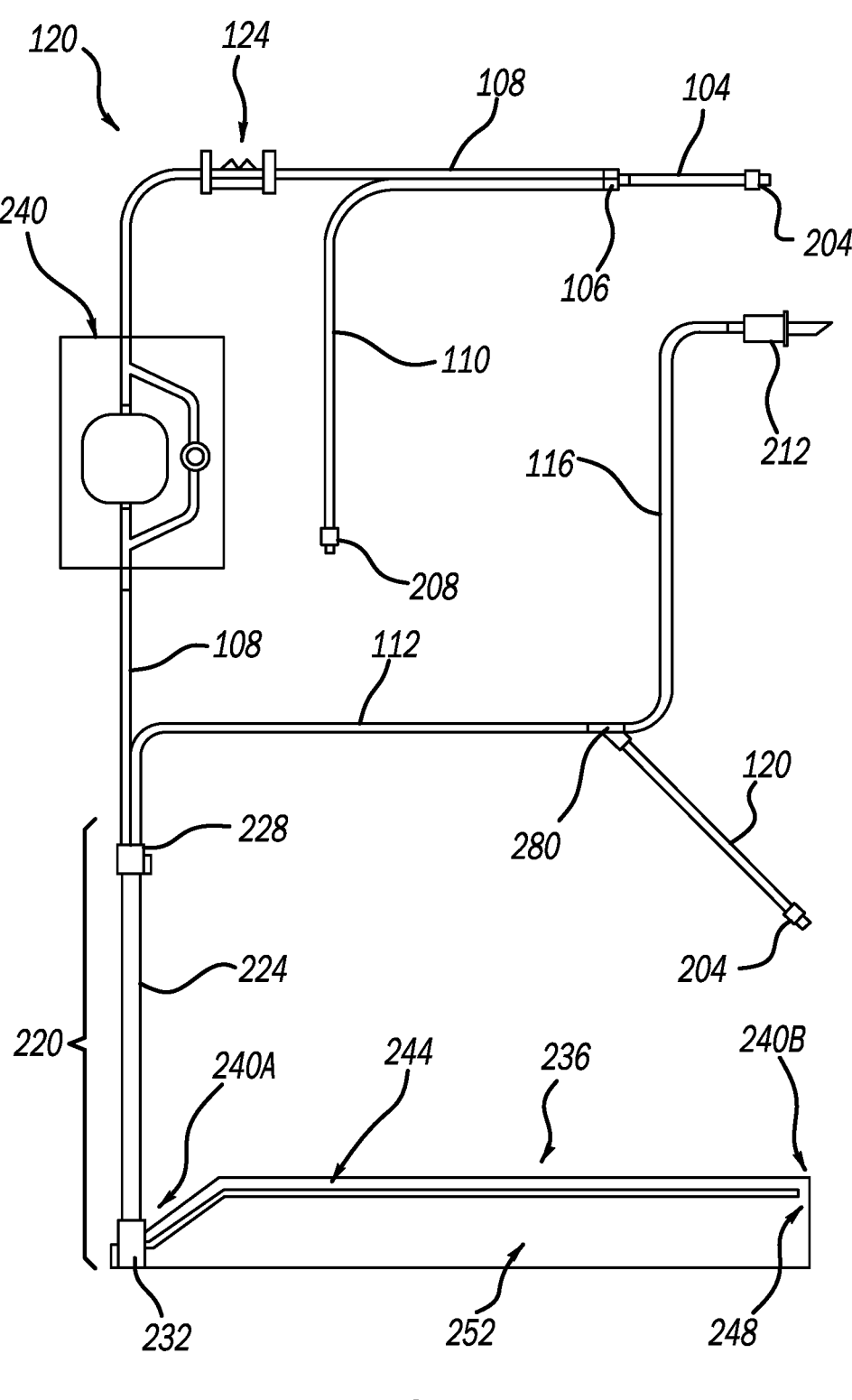
FIG. 2A shows a schematic view of a disposable tubing set including an integrated cuvette and prism in accordance with embodiments of the present disclosure.

FIG. 2A shows a schematic view of a disposable tubing set 120 including an integrated cuvette and prism 124 in accordance with embodiments of the present disclosure. The disposable tubing set 120 may include the tubing (e.g., one or more of the donor feed tubing 104, inlet tubing 108, anticoagulant tubing 110, loop exit tubing 112, saline tubing 116, plasma tubing 120, etc.), the connectors (e.g., one or more of the tubing connector 106, saline and plasma tubing y-connector 280, tubing fittings 204, tubing fitting 208, bag spike fitting 212, etc.), soft cassette 240, and the blood component collection loop 220.

The tubing may include any tubing having a central lumen configured to convey fluid therethrough. The tubing may be made from polyvinyl chloride (PVC), plasticized-PVC, polyethylene, ethylene with vinyl acetate (EVA), rubber, polymers, copolymers, and/or combinations thereof. The connectors may be configured to fluidly interconnect with the tubing (e.g., at one or more ends of the tubing, etc.). The connectors may insert into the central lumen of the tubing and/or attach to an outside of the tubing. In some embodiments, the connectors may be configured with various fittings (e.g., Luer fitting, twist-to-connect, and/or other small-bore couplings, etc.) to provide universal and/or reliable interconnections to one or more other fittings, connectors, tubing, needles, catheters, cannulas, and/or medical accessory. In one embodiment, the bag spike fitting 212 may be configured to insert into a receiving bag (e.g., a saline bag 118, etc.).

The blood component collection loop 220 may comprise a flexible loop 224 disposed between a system static loop connector 228 and a filler loop connector 232. The flexible loop 224 may be configured as a hollow flexible tube configured to receive and/or contain at least a portion of the inlet tubing 108 and the loop exit tubing 112. In some embodiments, the flexible loop 224 may be made from a thermoplastic elastomer having enhanced flexibility for transmitting twist from one end of the flexible loop 224 to the other. These types of elastomers may provide the flexibility of rubber while maintaining the strength and torque characteristics of plastics. Examples of the thermoplastic elastomer may include, but are in no way limited to, copolyester, DuPont™ Hytrel® thermoplastic elastomers, Eastman Neostar™ elastomers, Celanese Riteflex® elastomers. TOYOBO PELPRENE®, and/or other brand elastomers offering high flexibility and strength characteristics.

In some embodiments, the blood component collection loop 220 may include a blood component collection bladder 236 having a bladder loop end 240A and a bladder free end 240B. The blood component collection bladder 236 may include a first collection flow chamber 244 connected to the flexible loop 224 at the filler loop connector 232. In particular, fluid may flow between the inlet tubing 108 and the first collection flow chamber 244 via the flexible loop 224 and the connectors 228, 232, and/or vice versa. Fluid flowing in a direction from the bladder loop end 240A to the bladder free end 240B along the first collection flow chamber 244 may reach a flow chamber transition 248 and enter the second collection flow chamber 252. In one embodiment, the second collection flow chamber 252 is interconnected to the flexible loop 224 at the filler loop connector 232. In particular, fluid may flow between the loop exit tubing 112 and the second collection flow chamber 252 via the flexible loop 224 and the connectors 228, 232, and/or vice versa.

Figure 2B:
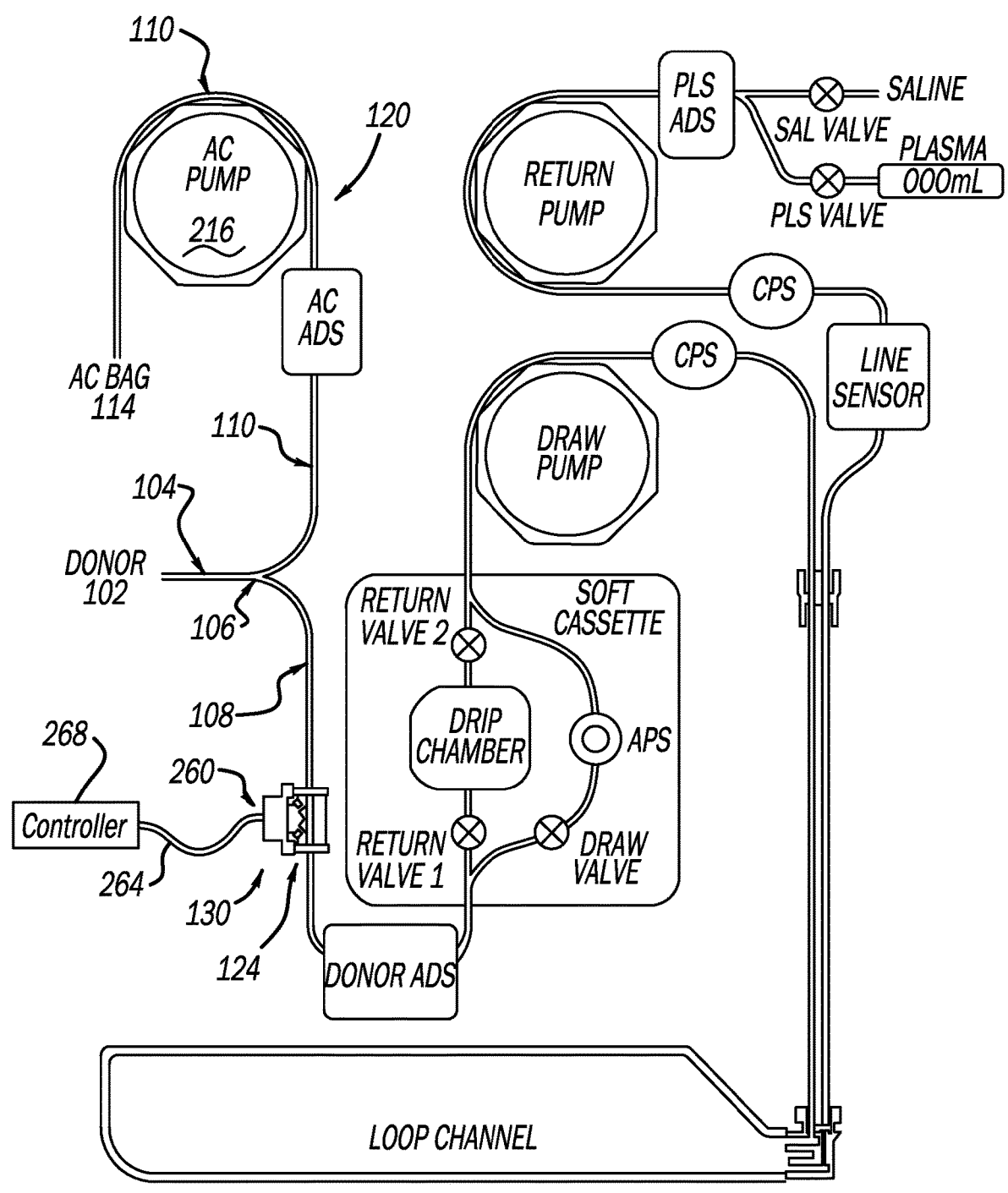
FIG. 2B shows a functional schematic diagram of the disposable tubing set of FIG. 2A engaged with an apheresis machine in accordance with examples of the present disclosure.

FIG. 2B shows a functional schematic diagram of the disposable tubing set 120 engaged with an apheresis system 100 in accordance with examples of the present disclosure. The description herein shows the components previously described, in FIGS. 1-2A, in a functional diagram to describe the interaction of the disposable tubing set 120 with the apheresis system 100 for extracting plasma or other blood components from the whole blood of a donor 102 during an apheresis procedure or process.

The apheresis system 100 can include an anticoagulant (AC) pump 216. The AC pump 216 pumps fluid in AC tubing 110 from the AC bag 114. The AC pump 216, the AC tubing 110, and/or the AC bag 114 may be as described previously. The AC tubing 110 may also include an AC air detection sensor (ADS) to detect air or fluid within the AC tubing 110. The AC ADS may be any light, ultrasonic, or other type of sensor that can detect the presence of fluid or air in the AC tubing 110 and provide that signal to a controller 268 of the apheresis system 100. Types of the AC ADS can include, for example, the SONOCHECK ABD05, made by SONOTEC US Inc., or another similar sensor. AC tubing 110 can intersect with and be fluidly associated with the donor feed tubing 104 and the inlet tubing 108 at tubing connector 106. The tubing connector 106 can be any type of connection between tubing 110, 104, and/or 108, as described previously.

The donor feed tubing 104 proceeds from the donor 102, where the donor 102 may be stuck with a lumen needle, cannula, catheter, or other device, allowing whole blood to flow from the donor 102 into the apheresis system 100 and allowing blood components to flow back to the donor 102. Tubing 108 may proceed to the integrated cuvette and prism 124. The integrated cuvette and prism 124 may correspond to a disposable plastic portion of the disposable tubing set 120 that is affixed to the tubing 108 of the disposable tubing set 120. When the disposable tubing set 120 is loaded into the apheresis system 100, the integrated cuvette and prism 124 may be engaged with a receiving space 130 of the apheresis system 100. The receiving space 130 may comprise kinematic attachment features that allow for accurate placement and location of the integrated cuvette and prism 124 inside the receiving space 130. The integrated cuvette and prism 124 may comprise an optically clear surface and a prism formed from the optically clear surface. In some examples, the prism and the optically clear surface may be formed from an integral piece of plastic. The optically clear surface of the integrated cuvette and prism 124 allows light to be emitted toward fluid contained inside the integrated cuvette and prism 124 and reflected light to be detected by the refractometer 260. The refractometer 260 may comprise a light source 262 (e.g., LED, etc.) that is configured to emit light toward the fluid in the integrated cuvette and prism 124 (e.g., through the prism to a first, lighted, side of the prism). As the emitted light interacts with the fluid in the integrated cuvette and prism 124, reflected light may be directed through the prism to a second, detecting, side of the prism onto a sensor 266 of the refractometer 260 (e.g., CCD, etc.). The reflected light may be directed onto the sensor at different angles depending on the fluid in the integrated cuvette and prism 124. The refractometer 260 may include a communications and power cable 264 running to and from a controller 268 (e.g., processor, etc.) of the apheresis system 100. The controller 268 may control operations of the refractometer 260 as described herein.

In some embodiments, the controller 268, or processor, may correspond to one or more computer processing devices. For example, the processor may be provided as silicon, an Application-Specific Integrated Circuit (ASIC), as a Field Programmable Gate Array (FPGA), any other type of Integrated Circuit (IC) chip, a collection of IC chips, and/or the like. In some embodiments, the processor may be provided as a Central Processing Unit (CPU), a microprocessor, or a plurality of microprocessors that are configured to execute the instructions sets stored in memory. Upon executing the instruction sets stored in memory, the processor enables various communications, activation of the light source, receiving light reflection detection information from the sensor, calibrating the refractometer 260, determining plasma protein levels, and/or interaction functions of the apheresis system 100, and may provide an ability to establish and maintain communication sessions between communication devices over the communication network when specific predefined conditions are met. The processor may be embodied as a virtual processor(s) executing on one or more physical processors. The execution of a virtual processor may be distributed over a number of physical processors or one physical processor may execute one or more virtual processors. Virtual processors are presented to a process as a physical processor for the execution of the process while the specific underlying physical processor(s) may be dynamically allocated before or during the execution of the virtual processor wherein the instruction stack and pointer, register contents, and/or other values maintained by the virtual processor for the execution of the process are transferred to another physical processor(s). As a benefit, the physical processors may be added, removed, or reallocated without affecting the virtual processors execution of the processes. For example, the processor may be one of a number of virtual processors executing on a number of physical processors (e.g., "cloud," "farm," array, etc.) and presented to the processes herein as a dedicated processor. Additionally or alternatively, the physical processor(s) may execute a virtual processor to provide an alternative instruction set as compared to the instruction set of the virtual processor (e.g., an "emulator"). As a benefit, a process compiled to run a processor having a first instruction set (e.g., Virtual Address Extension (VAX)) may be executed by a processor executing a second instruction set (e.g., Intel® 9xx chipset code) by executing a virtual processor having the first instruction set (e.g., VAX emulator).

As described above, the controller, or processor, may execute instruction sets stored in memory. The memory, or storage memory, may correspond to any type of non-transitory computer-readable medium. In some embodiments, the memory may comprise volatile or non-volatile memory and a controller for the same. Non-limiting examples of the storage memory that may be utilized in the apheresis system 100 and/or refractometer 260 may include Random Access Memory ("RAM"), Read Only Memory ("ROM"), buffer memory, flash memory, solid-state memory, or variants thereof. Any of these memory types may be considered non-transitory computer memory devices even though the data stored thereby can be changed one or more times. The memory may be used to store information about communications, identifications, conditional requirements, times, compliance, calibration settings, protein levels, historical data, and/or the like. In some embodiments, the memory may be configured to store rules and/or the instruction sets in addition to temporarily storing data for the processor to execute various types of routines or functions. Although not depicted, the memory may include instructions that enable the processor to store data into a memory storage device and retrieve information from the memory storage device. In some embodiments, the memory storage device or the data stored therein may be stored internal to the apheresis system 100 and/or refractometer 260 or in a separate server.

A donor air detection sensor can be placed on or in tubing 108 to detect the presence of fluid and/or air within tubing 108.

The soft cassette can include a first cassette port, which can function as, include, and/or be substantially proximate to a "Y" connector or section, or branches, that separates the tubing 108 into a first bypass branch and a first tubing section. The two tubing sections and can reconnect at a second cassette port, which can also function as, include, and/or be substantially proximate to a second "Y" connector or section. Tubing is bisected by the fluid sensor, which separates the tubing into the first bypass branch and the second bypass branch. Likewise, tubing is bisected by the drip chamber that separates tubing into a first tubing section and a second tubing section.

The first tubing section can include a first fluid control valve. The second tubing second can likewise include a second fluid control valve. The first bypass branch can similarly include a draw fluid control valve. As such, the various sections of tubing can be isolated by the valves based on the configuration of the apheresis system 100 and depending on the operation of the apheresis system 100.

A drip chamber may be disposed between the first tubing section and the second tubing section. The drip chamber can collect a volume of whole blood and/or high hematocrit blood (blood with a high percentage of red blood cells) depending on the operation of the apheresis system 100. The fluid sensor may be disposed between the first bypass branch and the second bypass branch.

Loop inlet tubing can connect to the second cassette port and can connect the soft cassette to the flexible loop 224, as described in conjunction with FIG. 2A. The loop inlet tubing may also include a sensor, disposed on or in the tubing, placed with the tubing before connecting with the system static loop connector 228 of the flexible loop 224. The pressure sensor (CPS) may detect one or more of, but not limited to: pressure, presence of fluid or air, and/or possibly another characteristic of the fluid in tube. Further, a draw pump can cause fluid to be pumped through tubing either away from the soft cassette or to the soft cassette.

Two or more different tubes can be connected to the flexible loop 224 through the system static loop connector 228 and provide fluid to, or receive fluid from, the blood component collection bladder 236. A loop exit tubing 112 exits the system static loop connector 228 from flexible loop 224. This loop exit tubing 112 can also include another line sensor disposed thereon or therein to detect fluid, air, cellular concentration, color, and/or color change in the fluid coming from the flexible loop 224; the line sensor can be the same or similar in type and/or function to the sensors previously described. A second CPS sensor or fluid sensor may also be disposed in or on line 112. Sensor may detect one or more of, but not limited to: the presence or absence of fluid, pressure within tubing 112, and/or other characteristic of the fluid in tubing 112. Similarly, sensor can be the same or similar in type and/or function to sensors previously described.

Loop exit tubing 112 may then flow into a plasma air detection sensor before the saline and plasma tubing y-connector 280 separates the tubing 112 into saline tubing 116 and plasma tubing 120. The return pump 212 may interact with the loop exit tubing 112 and can cause fluid or air to flow through tubing 112 from either the flexible loop 224 or from a saline bag 118 and/or a plasma collection bottle 122.

The saline bag 118 and associated tubing can be as previously described and can provide saline through the system 200 back to the donor 102. A saline flow control valve 288 can isolate the saline bag 118 from the rest of the system 200. Further, a plasma collection bottle 122 can receive plasma from the flexible loop 224 when processed or separated from the whole blood. The plasma collection bottle 122 can be selectively isolated from the system by the plasma flow control valve.

Figure 3A:
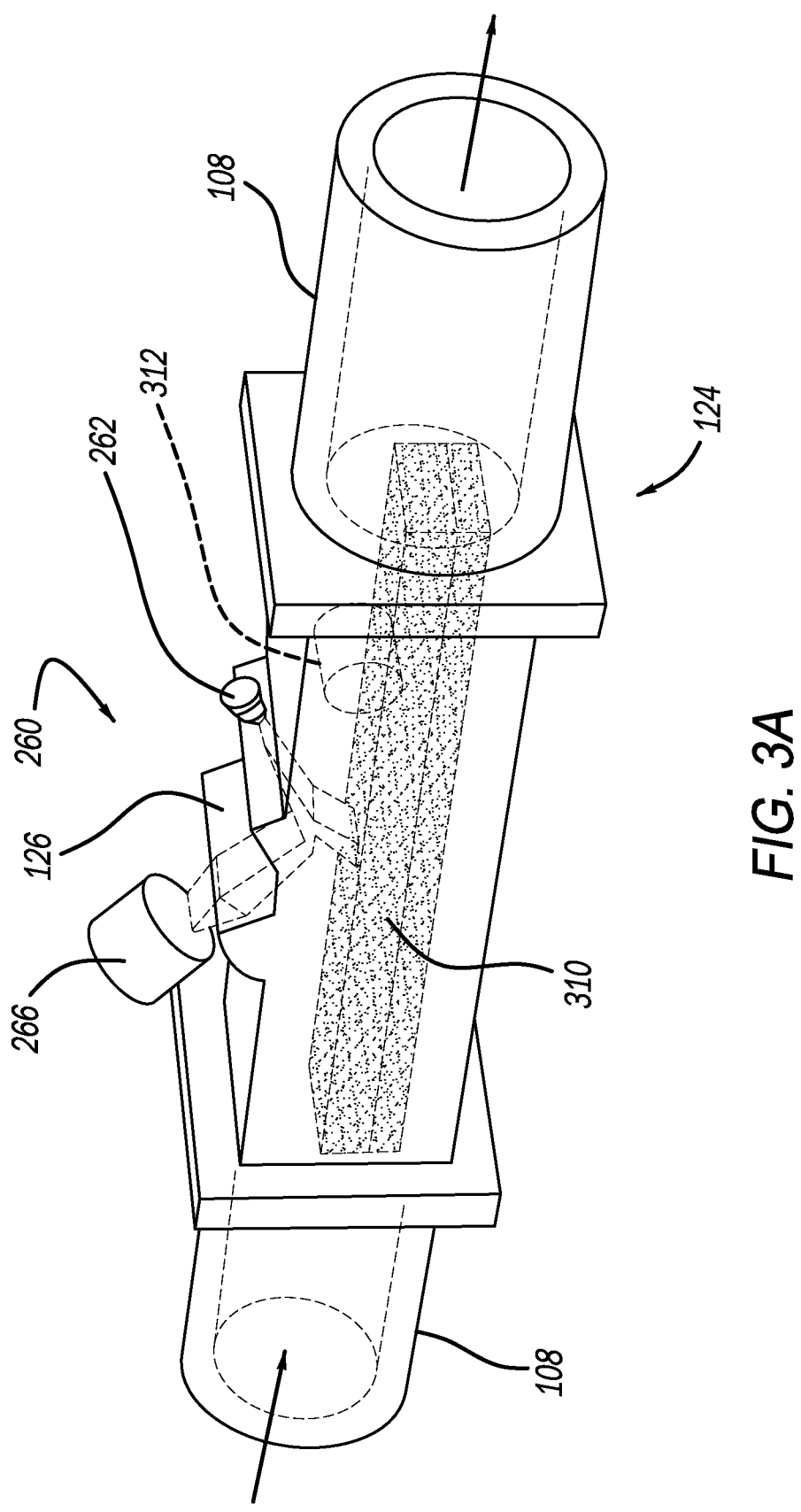
FIG. 3A shows a detail perspective view of an integrated cuvette and prism of the disposable tubing set and a separate refractometer in accordance with embodiments of the present disclosure.

FIG. 3A shows a detail perspective view of an integrated cuvette and prism 124 of the disposable tubing set 120 and a separate refractometer 260 in accordance with embodiments of the present disclosure. As illustrated in FIG. 3A, the integrated cuvette and prism 124 may be affixed to the tubing 108, forming a part of the disposable tubing set 120. For example, after the apheresis procedure is completed, the entire disposable tubing set 120 including the integrated cuvette and prism 124 may be discarded. Stated another way, the disposable tubing set including the integrated cuvette and prism 124 may be designed for a single use only.

The integrated cuvette and prism 124 may include an integrated prism that is formed from a surface of the integrated cuvette and prism 124. In one example, the prism and the portions of the integrated cuvette and prism 124 may be injection molded as an integral piece. As whole blood flows along the fluid flow path of the tubing 108, the whole blood may enter a portion of the integrated cuvette and prism 124 that is disposed adjacent the refractometer 260. The refractometer 260 is shown in FIG. 3A without the housing and engagement features for the sake of clarity in disclosure. Rather, the light source (e.g., LED) and the sensor (e.g., CCD) of the refractometer 260 are shown emitting light 262 toward the whole blood (through the integrated prism of the integrated cuvette and prism 124) and receiving reflected light from the whole blood (through the integrated prism of the integrated cuvette and prism 124), respectively. The refractometer 260 may be configured to measure protein levels in the whole blood while flowing along the fluid flow path through the integrated cuvette and prism 124. These measurements may be made even at flow rates of up to 200 mL/min.

Figure 3B:
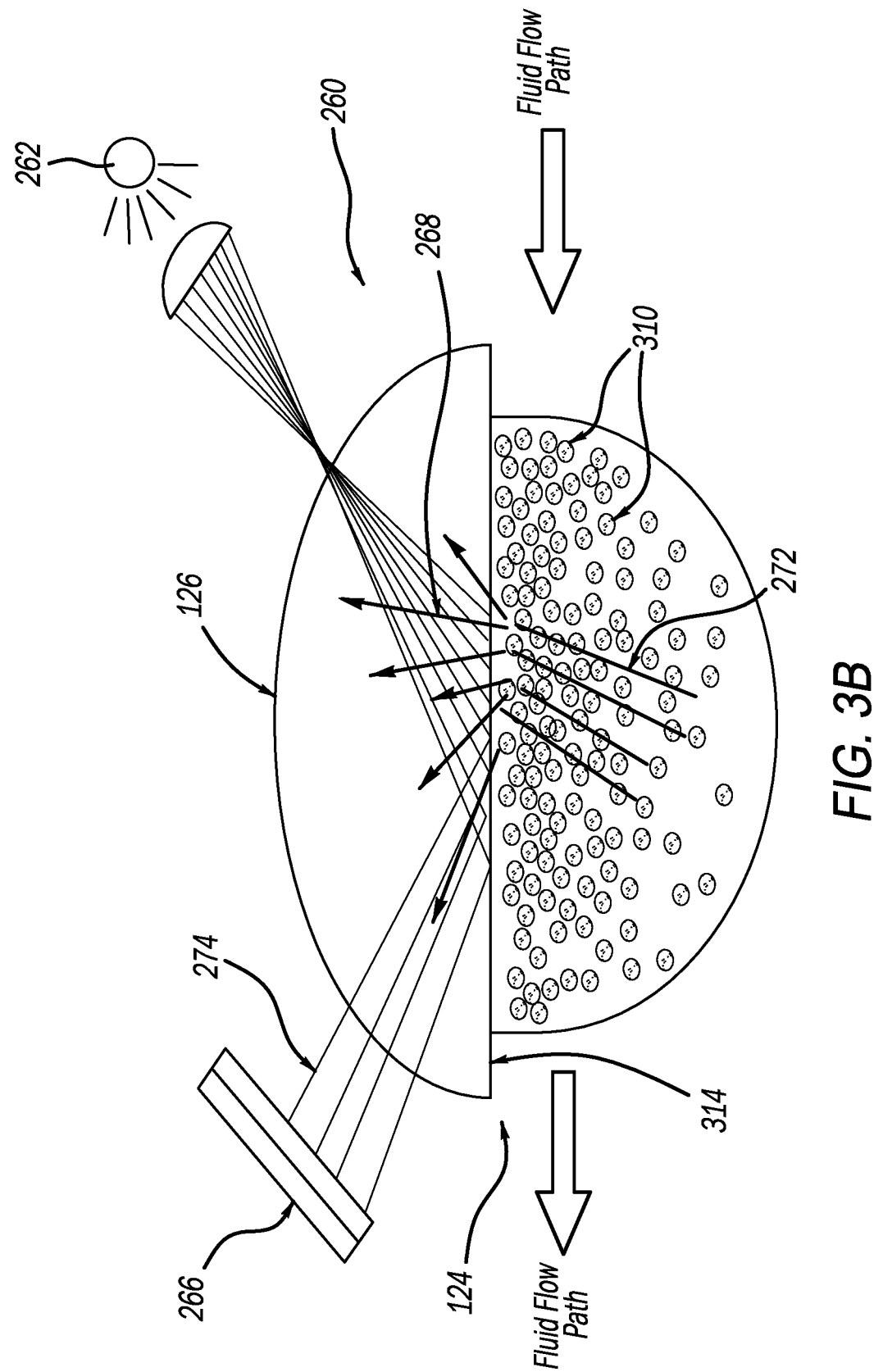
FIG. 3B shows a schematic optical diagram of the refractometer operating with the integrated cuvette and prism of the disposable tubing set in accordance with embodiments of the present disclosure.

In some examples, ultrasonic separators (e.g., ultrasonic transducers, piezoelectric transducers, etc.) 312 (FIG. 3A) may be disposed adjacent at least one side of the integrated cuvette and prism 124. The ultrasonic separators may be activated (e.g., by the controller, etc.) to accelerate settling of red blood cells 310 away from the sensing surface of the integrated cuvette and prism 124. This accelerated settling occurs when orientation of the assembly is such that gravity draws cells away from the sensing surface 314 (FIG. 3B). In one example, the integrated cuvette and prism 124 may be oriented such that the integrated prism is located on a side of the integrated cuvette and prism 124 that is facing away from gravity (e.g., a gravity vector, etc.). For instance, the integrated prism 126 may be arranged on a top side of the integrated cuvette and prism 124 allowing gravity to assist in forcing red blood cells 310 to settle away from the sensing surface, providing a clearer refractive response from the plasma in the whole blood. As depicted and due to gravitational forces, the red blood cells 310 shown in FIG. 3B, would move away from the sensing surface of the integrated cuvette and prism 124. Also pausing the flow of whole blood being analyzed advantageously allows gravity to pull red blood cells away from the sensing surface, which reduces the amount of light reflected by the red blood cells and improves the reading of the sensor of the refractometer 260.

FIG. 3B shows a schematic optical diagram of the refractometer 260 operating with the integrated cuvette and prism 124 of the disposable tubing set 120 in accordance with embodiments of the present disclosure. As the whole blood passes over the sensing surface of the integrated cuvette and prism 124, the refractometer 260 may emit light from the light source toward the whole blood on the sensing side of the integrated prism. Some of the emitted light may be refracted light 272 that passes into the whole blood and some of the emitted light may be reflected from the sensing surface toward the sensor 266 as reflected light 274. Depending on the plasma protein level of the whole blood, a modified (as compared to the anticoagulant) pixel intensity pattern is sensed by the light sensor 266 (e.g. CCD). The modified pixel intensity pattern of the whole blood is then compared to the baseline pattern of the anticoagulant solution and the plasma protein concentration is determined based on the differences in pixel intensity patterns (as described further herein).

In some examples, the light source 262 may be caused to emit light at a specific wavelength, or wavelengths, to provide more accurate results of protein level measurements of the whole blood. For instance, the light source may emit light at 420 nm, which may allow the red blood cells to absorb refracted light rather than reflect the light toward the sensor. In this manner, the reflected light interference 268 from the red blood cells on plasma protein level measurements may be mitigated, or even eliminated. In other words, when the light source is configured to emit light at 420 nm, the reflected light 268 off the red blood cells illustrated in FIG. 3B will be eliminated because the 420 nm light will be absorbed by the red blood cells.

Figure 4:
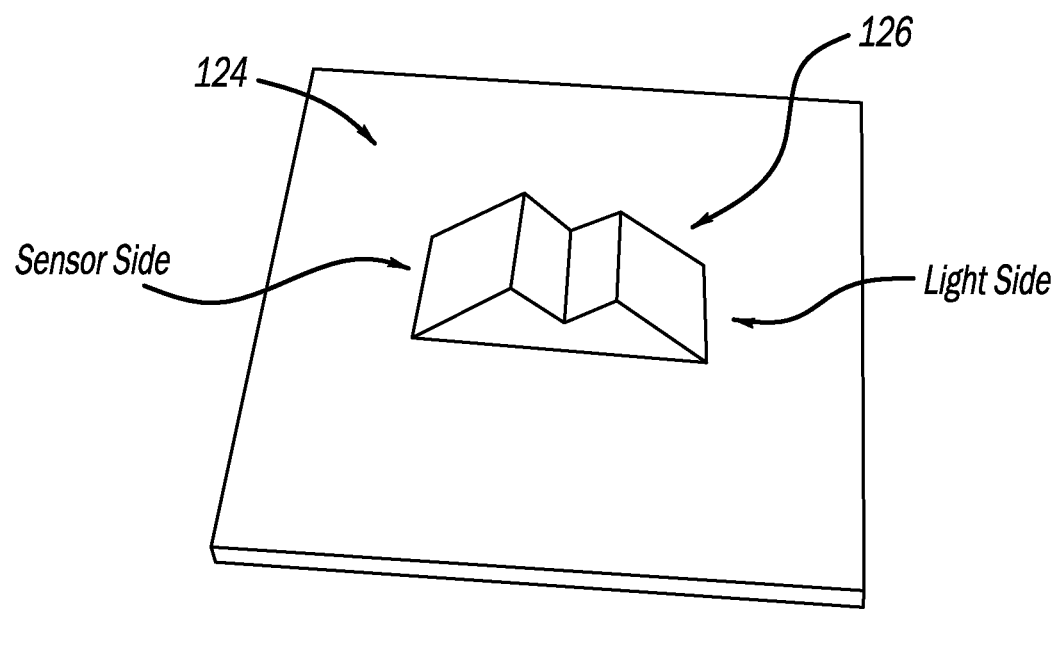
FIG. 4 shows a perspective view of a prism formed in an integrated cuvette substrate in accordance with examples of the present disclosure.

FIG. 4 shows a perspective view of an integrated prism 126 formed in an integrated cuvette substrate sample in accordance with examples of the present disclosure. The integrated prism 126 of the integrated cuvette and prism 124 may be made of any suitable material. For example, the prism 126 may be injection molded from a plastic material (polyethylene terephthalate glycol or polycarbonate, for example), or may be made of glass. The plastic material may provide a clear optical path from outside of the integrated prism 126 to an inner chamber of the integrated cuvette and prism 124 through which the whole blood is being channeled. The integrated prism 126 may have any suitable shape. For example, the integrated prism 126 may be formed in the shape of a triangular prism, an M-shaped prism, a prism having at least one triangular prism portion and at least one curved (e.g., concave and/or convex) surface, etc., and/or combinations thereof. In any event, the integrated prism may comprise a sensor side and a light side. As illustrated in FIG. 2B, for example, when the integrated cuvette and prism 124 of the disposable tubing set 120 is engaged with the receiving space 130 of the apheresis system 100, the light side (LS) may be disposed adjacent the light source of the refractometer 260 and the sensor, or detector, side (DS) may be disposed adjacent the sensor of the refractometer 260. In some examples, the light source may be separate, and offset a distance, from the sensor of the refractometer 260.

Figure 5:
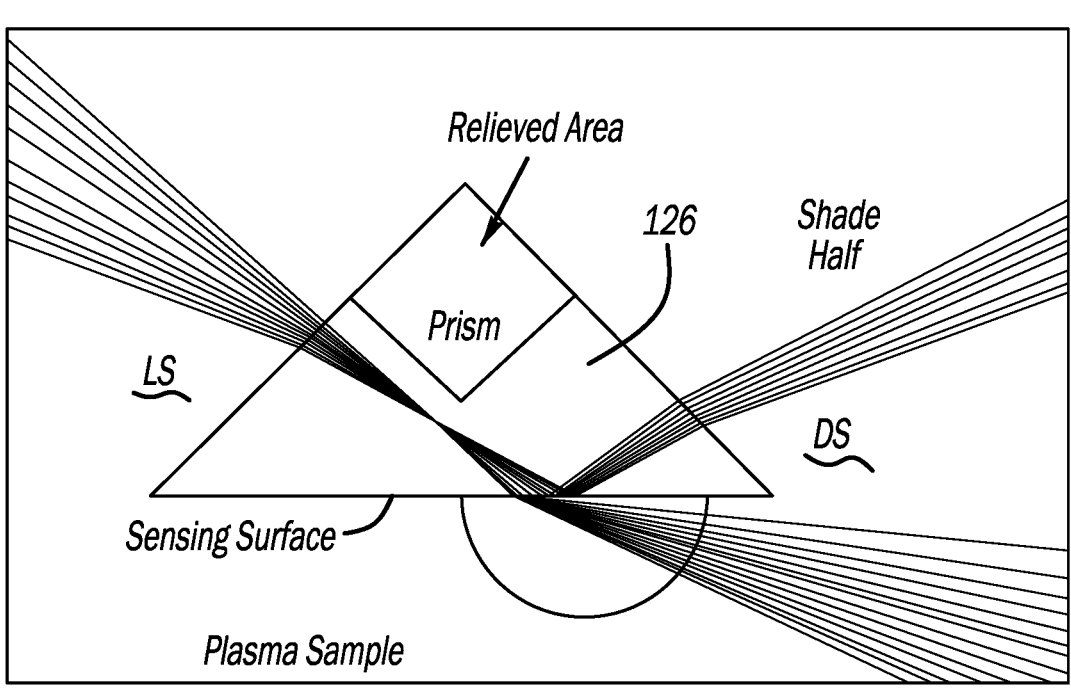
FIG. 5 shows a schematic optical diagram of light refracting through a plasma sample and reflecting from the prism sensing surface to a detection side of a prism in accordance with examples of the present disclosure.

As shown in the schematic optical diagram of FIG. 5, the M-shaped prism 126 may include a relieved area between the light side, LS, and detector side, DS, of the integrated prism. This relieved area may decrease the amount of material required for the integrated prism, provide enhanced molding characteristics, and/or provide clearance for engagement with a portion of a refractometer 260. FIG. 5 shows light being emitted from the light side, LS, and then a portion being refracted into and through a plasma sample and a remaining portion being reflected from the sensing surface to a detector side, DS, of a prism.

Figure 6A:
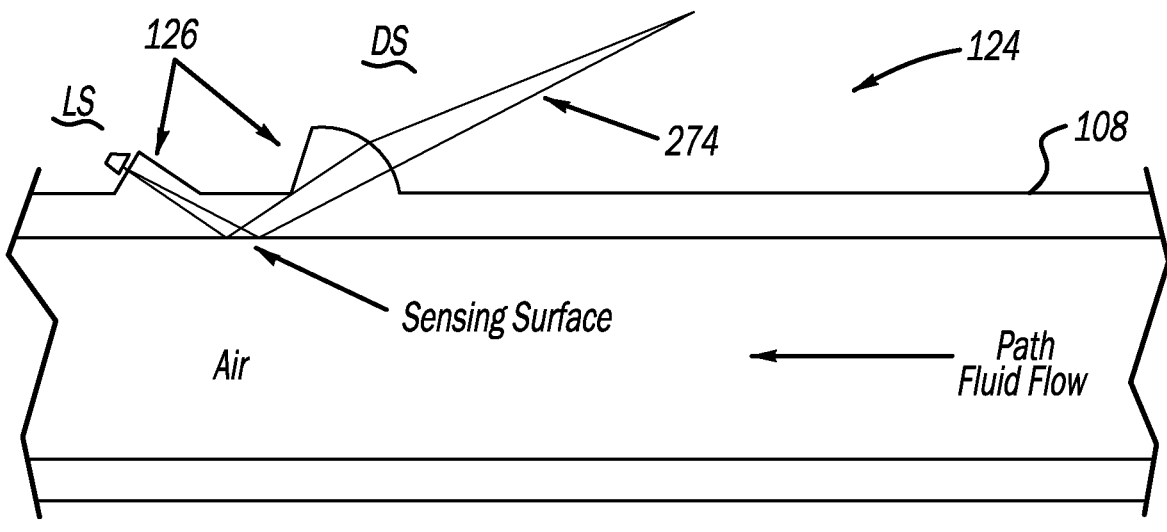
FIG. 6A shows a schematic optical diagram of light reflecting from a sensing surface of an integrated cuvette containing air to a detection side of a prism of the integrated cuvette in accordance with examples of the present disclosure.
Figure 6B:
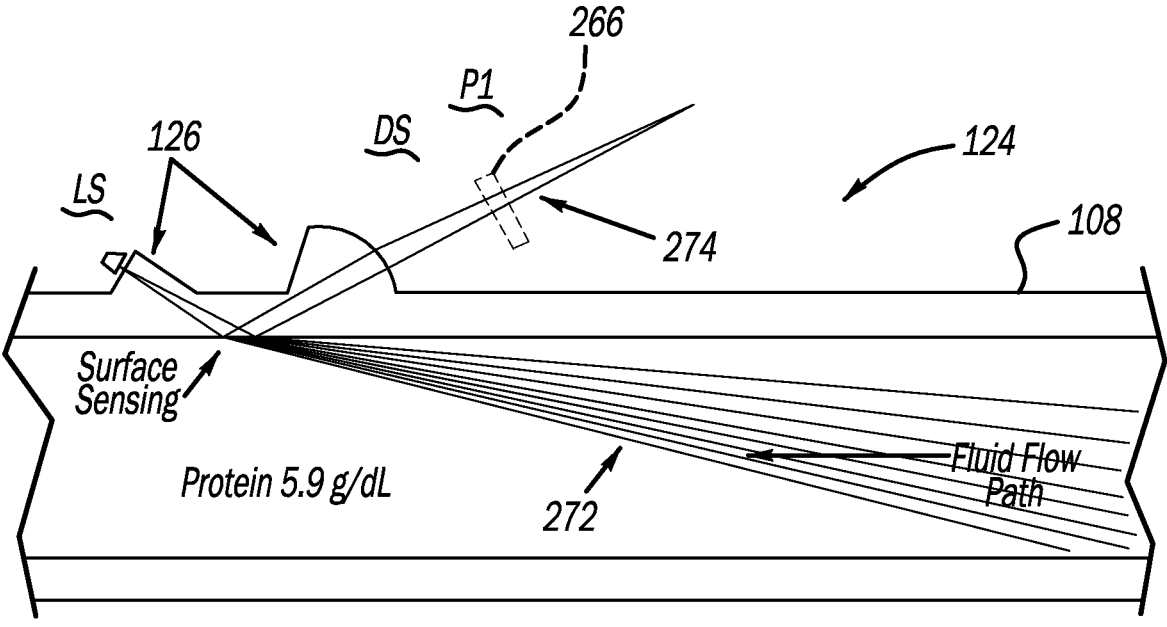
FIG. 6B shows a schematic optical diagram of light reflecting from a sensing surface of an integrated cuvette containing whole blood having a first plasma protein to a detection side of a prism of the integrated cuvette in accordance with examples of the present disclosure.
Figure 6C:
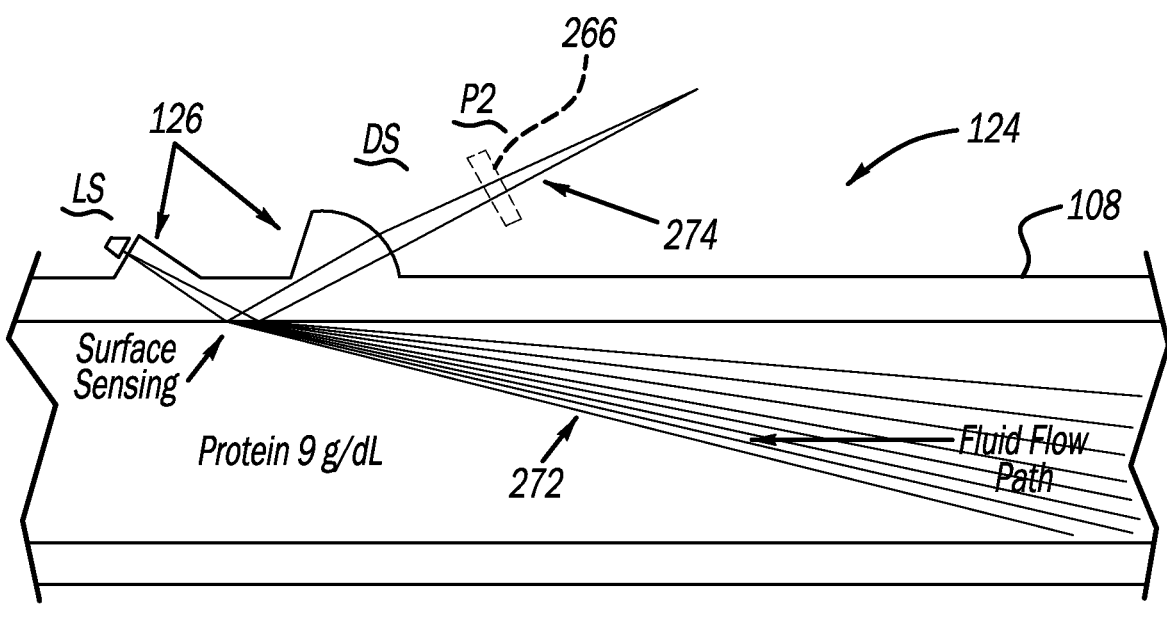
FIG. 6C shows a schematic optical diagram of light reflecting from a sensing surface of an integrated cuvette containing whole blood having a second plasma protein to a detection side of a prism of the integrated cuvette in accordance with examples of the present disclosure.

FIGS. 6A-6C show schematic optical diagrams of light being emitted from a light side, LS, of the integrated prism through a first portion of the integrated prism (e.g., having a triangular prism shape) and reflecting in a direction from a sensing surface of the integrated cuvette and prism 124 through a second portion of the integrated prism (e.g., having a semi-curved shape) to a detector side, DS, of the integrated cuvette and prism 124 in accordance with examples of the present disclosure.

In the schematic optical diagram of FIG. 6A, the tubing 108 comprises air and all of the light from the source reflected to the detector side with no light being refracted. In FIG. 6B, the tubing 108 comprises whole blood having a plasma protein level of 6.0 g/dL conveyed to the integrated cuvette and prism 124. In this example, the light reflected to the detector side is reflected onto the sensor (shown in dashed lines) to generate a pixel intensity pattern that illuminates pixels in a first pixel position region, P1. In FIG. 6C, the tubing 108 comprises whole blood having a plasma protein level of 9.0 g/dL conveyed to the integrated cuvette and prism 124. The light reflected to the detector side in FIG. 6C is reflected onto the sensor (shown in dashed lines) to generate a pixel intensity pattern that illuminates pixels in a second pixel position region, P2. When whole blood is measured by the refractometer 260 and produces reflected light that falls between, and including, these two limits (e.g., P1 and P2), the donor 102 is eligible to donate plasma and apheresis may be automatically started (e.g., without further setup, connection, etc.). However, in the event that the whole blood is measured by the refractometer 260 to produce reflected light that falls outside of these two limits (e.g., P1 and P2), the donor 102 is determined to be ineligible to donate plasma and the apheresis process is automatically prevented from starting. In some examples, an alarm may be emitted along with a message conveying the ineligibility of the donor 102 and/or information about the measured plasma protein level.

Figure 7:
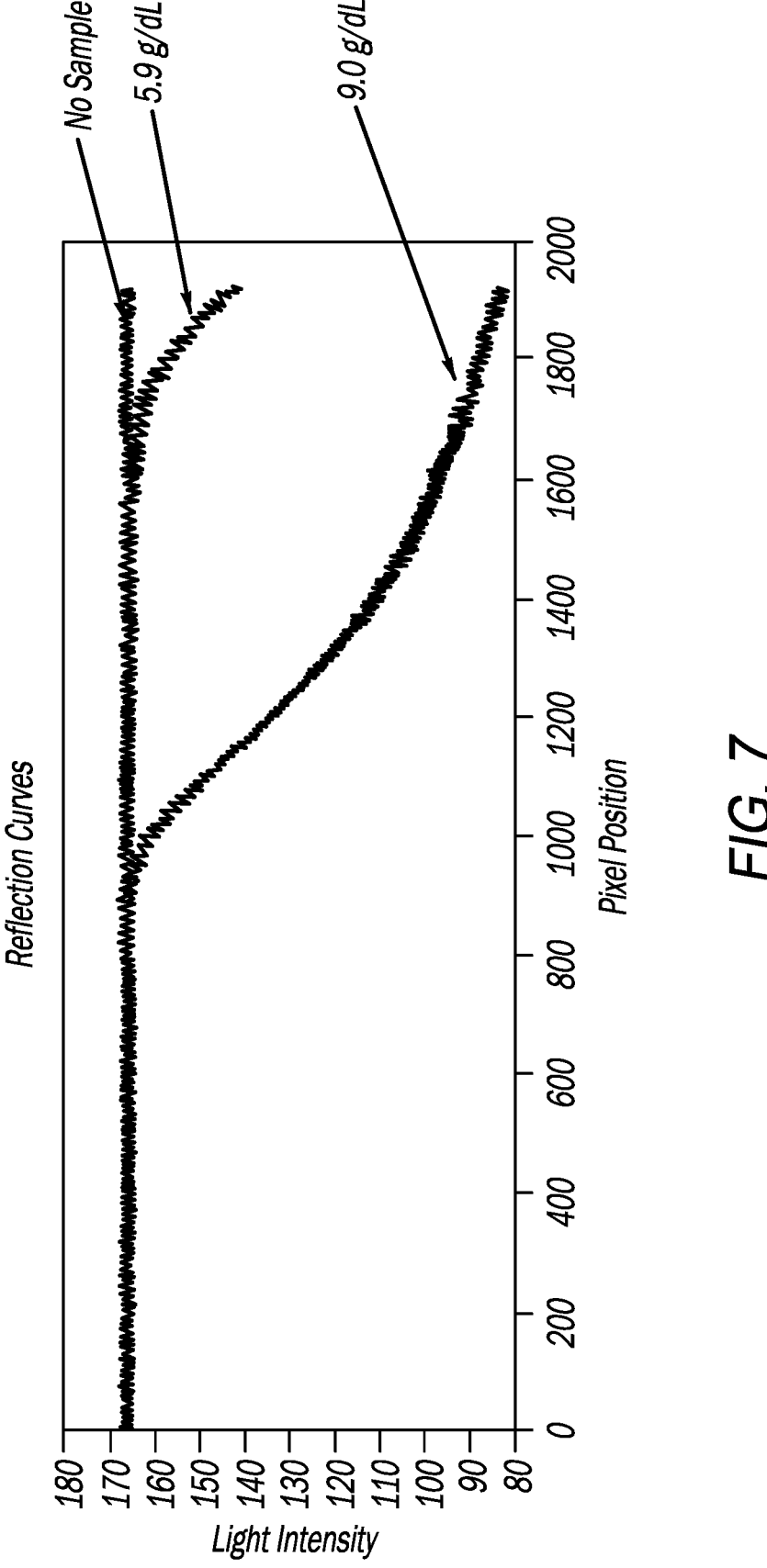
FIG. 7 shows a graph of light intensity versus pixel position measured by a sensor of the refractometer detecting reflectivity of various fluids in accordance with examples of the present disclosure.

FIG. 7 shows a graph of light intensity versus pixel positions measured by a sensor of the refractometer 260 detecting reflected light from various fluids in accordance with examples of the present disclosure. In some examples, the "no sample" line may correspond to a baseline or reference value that is associated with total reflection of source light when air is against the prism sensing surface (as depicted in FIG. 6A). By using anticoagulant to establish a calibration reference value, the refractometer 260 may determine the shift in pixel positions between the anticoagulant and the whole blood test sample. The anticoagulant pixel position of a selected light intensity value is determined. When the whole blood sample is placed into the cuvette, the pixel position reporting the selected light intensity value is determined. The difference between these two pixel positions (herein termed "pixel shift") is proportional to the plasma protein content. For example, and as shown in FIG. 7, which depicts pixel intensities from two a whole blood samples where one sample contains a plasma protein level of 5.9 g/dL and the second sample contains a plasma protein level of 9.0 g/dL. In the 5.9 g/dL sample, the reflected light may illuminate pixel position 1800 of a sensor at light intensity of about 158. In a whole blood sample where the plasma protein level is 9.0 g/dL, the pixel position illuminated to a light intensity of 158 has shifted to position 1020. The shift in pixel positions of equivalent intensities (Pixel Shift=1800-1020) is proportional to the difference in plasma protein levels. Among other things, this proportionality and method allow the refractometer 260 to be calibrated using a known solution, such as anticoagulant for example which simulates a plasma protein content of 2.4 g/dL, each time a new integrated cuvette and prism 124 of the disposable tubing set 120 is engaged with the apheresis system 100. Thus, any manufacturing inconsistencies, or inconsistencies in how the integrated cuvette and prism 124 is seated in the receiving space 130, do not negatively impact accuracy of the test results because such inconsistencies are effectively negated by comparing pixel shift between sensor pixels illuminated by light reflected off anticoagulant with sensor pixels illuminated by light reflected off the whole blood being tested.

Figure 8:
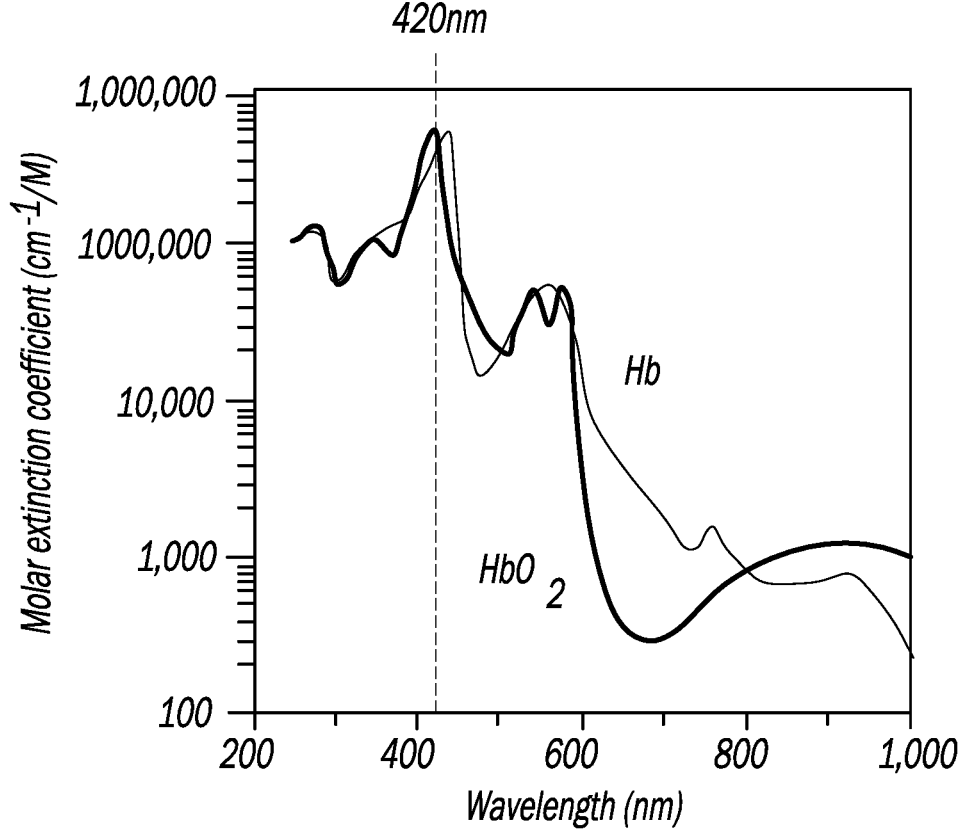
FIG. 8 shows a graph of the absorption of light by red blood cells at various wavelengths in accordance with examples of the present disclosure.

FIG. 8 shows a graph of the absorption of light by red blood cells at various wavelengths in accordance with examples of the present disclosure. As shown in the graph of FIG. 8, the absorption of light is greatest in red blood cells at 420 nm. Setting the light source, or LED, of the refractometer 260 to emit light at 420 nm can reduce interference in measurements of whole blood. For instance, the light refracted from the light source at 420 nm may be absorbed, not reflected and scattered, by the red blood cells. However, the 420 nm light from the source may still be reflected from the prism sensing surface due to the presence of the plasma in the whole blood. In some cases, use of a 420 nm light source may cause reflection and scatter of light from the red blood cells to be mitigated or even eliminated from measurement by the sensor of the refractometer. Other suitable wavelengths for light emitted by the refractometer, which may be absorbed by red blood cells, include, but are not limited to, about 275 nm, about 375 nm, and within the range of about 550 nm-600 nm.

Figure 9:
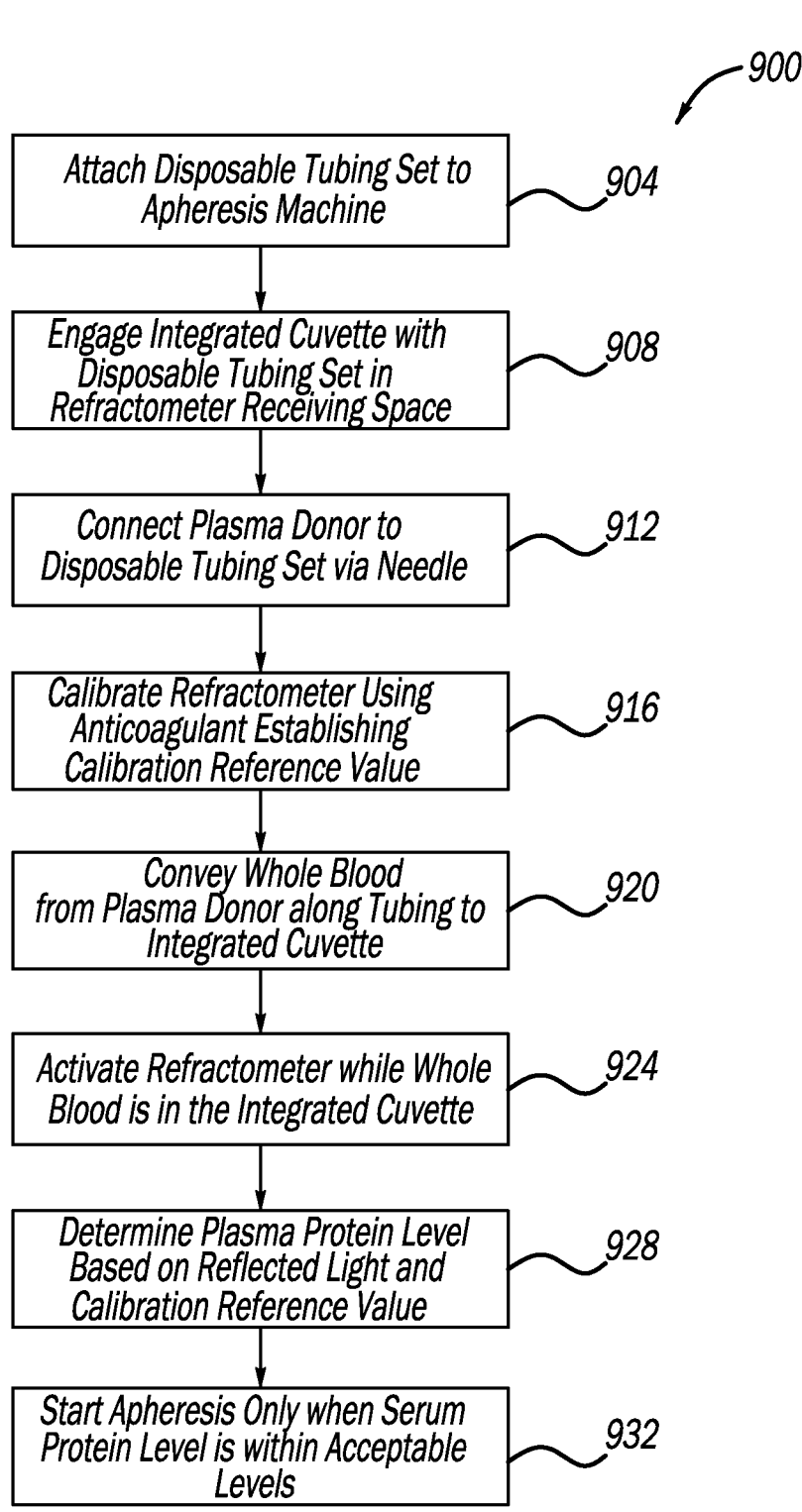
FIG. 9 is a flow diagram of a method for automatically performing inline testing of protein levels of whole blood obtained from a plasma donor connected to an apheresis machine in accordance with embodiments of the present disclosure.

FIG. 9 is a flow diagram of a method 900 for automatically performing inline testing of protein levels of whole blood obtained from a donor 102 connected to an apheresis system 100 in accordance with embodiments of the present disclosure. A general order for the steps of the method 900 is shown in FIG. 9. Generally, the method 900 begins at step 904 and ends at step 932. The method 900 can include more or fewer steps or can arrange the order of the steps differently than those shown in FIG. 9. The method 900 can be, at least partially, executed as a set of computer-executable instructions executed by a computer system, controller, processor, centrifuge microcontroller, and/or another device and encoded or stored on a computer readable medium. In other configurations, the method 900 may be executed, at least partially, by a series of components, circuits, gates, etc. created in a hardware device, such as a System on Chip (SOC), Application Specific Integrated Circuit (ASIC), and/or a Field Programmable Gate Array (FPGA). Hereinafter, the method 900 shall be explained with reference to the systems, devices, valves, pumps, sensors, components, circuits, modules, software, data structures, signaling processes, models, environments, apheresis systems, etc. described in conjunction with FIGS. 1-8.

The method 900 may begin by attaching a disposable tubing set 120 to an apheresis machine, or system, 100 (step 904). In this step the tubing of the disposable tubing set 120 may be inserted into receiving areas of the apheresis system 100 and engaged with pumps, valves, bags, collection containers, and/or the like.

Next, the integrated cuvette and prism 124 is engaged with a refractometer receiving space 130 of the apheresis system 100 (step 908). In some examples, engaging the integrated cuvette and prism 124 may include clamping a body of the integrated cuvette and prism 124 into a recessed area of the apheresis system 100. The receiving space 130 may comprise one or more kinematic features that accurately align the integrated cuvette and prism 124 of the disposable tubing set 120 relative to the refractometer 260 of the apheresis system 100. In one example, the integrated cuvette and prism 124 may be placed into a bracket or holder of the apheresis system 100 in the receiving space 130 and a lid, or door, may enclose the integrated cuvette and prism 124 inside the receiving space 130. The door may apply pressure to the integrated cuvette and prism 124 forcing at least one surface of the integrated cuvette and prism 124 against a support surface in the receiving space 130. In some examples, the door may be held shut with a knob, clamp, magnet, and/or latch.

The method 900 may continue by connecting a donor 102 to the disposable tubing set 120 (step 912). In some examples, this connection may include inserting a needle, catheter, or cannula into a vein of the donor 102 (e.g., in the arm of the donor 102) and ensuring that blood is able to flow from the donor 102 along the donor feed tubing 104. The donor 102 may remain connected to the disposable tubing set 120 while the apheresis system 100 operates.

Before starting the apheresis process, the method 900 proceeds by calibrating the refractometer 260 associated with the apheresis system 100 (step 916). The calibration allows different disposable tubing sets 120 having an integrated cuvette and prism 124 to be engaged with the apheresis system 100 and a baseline, or calibration reference value, to be established for the integrated cuvette and prism 124 that is unique to the disposable tubing set 120. Additional details regarding calibration are disclosed in conjunction with FIG. 10.

Once calibrated, the method 900 may continue by pumping whole blood from the donor 102 to the integrated cuvette and prism 124 (step 920). For instance, following the fluid paths illustrated in FIG. 2B, the draw pump may cause whole blood to be drawn from the donor 102 along the donor feed tubing 104, through the tubing connector 106, and along the inlet tubing 108, and into, and through, the integrated cuvette and prism 124 (step 920). In some examples, the integrated cuvette and prism 124 may be affixed to the inlet tubing downstream from the tubing connector and upstream from the soft cassette. When connected to the apheresis system 100, the integrated cuvette and prism 124 may also be located upstream from other pumps. The integrated cuvette and prism 124 is oriented adjacent the refractometer 260 comprising the light source and the sensor.

Next, the method 900 continues by activating the refractometer 260 while whole blood is in the integrated cuvette and prism 124 (step 924). In some examples, the refractometer 260 may be activated while the whole blood passes through the integrated cuvette and prism 124 from one end of the integrated cuvette and prism 124 to the other end of the integrated cuvette and prism 124. In some examples, flow may be stopped when whole blood fills a chamber of the integrated cuvette and prism 124. Activating the refractometer may include causing the light source to emit light at 420 nm in a direction toward the integrated cuvette and prism 124 and, more specifically, through the integrated prism and onto the whole blood contained therein. As the light is emitted, the sensor may detect reflected light on one or more pixels, pixel regions, and/or pixel locations.

Based on the reflected light and the calibration reference value, the method 900 may proceed to determine the plasma protein levels in the whole blood (step 928). For instance, the reflected light caused by the whole blood may project a modified pixel intensity pattern, as compared to the anticoagulant calibration reference pattern, onto the sensor. The shift in pixel pattern between the calibration solution and whole blood may be used to determine the plasma protein content of the whole blood. Additional details regarding this determination are disclosed in conjunction with FIG. 11 and FIGS. 12A-12G.

When the plasma protein levels are determined to be within predetermined "acceptable" limits of 6.0 g/dL to 9.0 g/dL, for example, the donor 102 is considered eligible to donate plasma and the apheresis process is automatically started by the apheresis system (step 932). This apheresis process can be started automatically without further machine setup or processing of the donor 102, the apheresis system 100, and/or changing connections to the donor 102. However, if the plasma protein level is determined to be outside of the predetermined acceptable limits (e.g., lower than 6.0 g/dL or higher than 9.0 g/dL), the donor 102 is considered to be ineligible to donate plasma and the apheresis process is prevented from starting. In this latter case, the disposable tubing set 120 is removed from the apheresis system 100 and discarded (e.g., disposed of). Since the methods and systems described herein allow for measurements and apheresis to be performed in a single setup (e.g., inline) there is less waste (e.g., labor to obtain plasma protein content, no finger-prick needles, capillary tubes, etc., that need to be used) and there are fewer steps to be performed (e.g., no obtaining a separate sample, centrifuging the sample, and then testing the sample using a handheld refractometer, etc., prior to connecting a donor 102 to the apheresis system 100). As can be appreciated, the present disclosure allows for efficient and cost effective processing of donors 102 through apheresis.

FIG. 10 is a flow diagram of a method 1000 for automatically calibrating the refractometer 260 associated with the apheresis system 100 in accordance with embodiments of the present disclosure. The method 1000 may correspond to step 916 described in conjunction with FIG. 9. A general order for the steps of the method 1000 is shown in FIG. 10. Generally, the method 1000 begins at step 1004 and ends at step 1020. The method 1000 can include more or fewer steps or can arrange the order of the steps differently than those shown in FIG. 10. The method 1000 can be, at least partially, executed as a set of computer-executable instructions executed by a computer system, controller, processor, centrifuge microcontroller, and/or another device and encoded or stored on a computer readable medium. In other configurations, the method 1000 may be executed, at least partially, by a series of components, circuits, gates, etc. created in a hardware device, such as a System on Chip (SOC), Application Specific Integrated Circuit (ASIC), and/or a Field Programmable Gate Array (FPGA). Hereinafter, the method 1000 shall be explained with reference to the systems, devices, valves, pumps, sensors, components, circuits, modules, software, data structures, signaling processes, models, environments, apheresis systems, methods, etc. described in conjunction with FIGS. 1-9.

The method 1000 may begin by flowing anticoagulant from the AC bag 114 through the AC tubing 110 and to the integrated cuvette and prism 124 (step 1004). For instance, referring to the schematic diagram of FIG. 2B, the AC pump may pump the anticoagulant from the AC bag 114 through the AC tubing 100 and then through the tubing connector 106 to be conveyed along the inlet tubing 108 into, and through, the integrated cuvette and prism 124. In some examples, the integrated cuvette and prism 124 may be affixed to the inlet tubing downstream from the tubing connector and upstream from the soft cassette. When connected to the apheresis system 100, the integrated cuvette and prism 124 may also be located upstream from other pumps. The integrated cuvette and prism 124 is oriented adjacent the refractometer 260 comprising the light source and the sensor.

Next, the method 1000 may continue by activating the refractometer 260 while anticoagulant is present in a chamber of the integrated cuvette and prism 124 (step 1008). In some examples, the refractometer 260 may be activated while the anticoagulant continues to pass through the integrated cuvette and prism 124 from one end of the integrated cuvette and prism 124 to the other end of the integrated cuvette and prism 124. In some examples, flow may be stopped when anticoagulant fills the inner chamber of the integrated cuvette and prism 124. Activating the refracto-meter 260 may include causing the light source to emit light at 420 nm in a direction toward the integrated cuvette and prism 124 and, more specifically, through the integrated prism and onto the anticoagulant contained therein.

The method 1000 may continue when emitted light is reflected from the prism sensing surface and the reflected light is received at the sensor of the refractometer 260 (step 1012). The sensor may correspond to a CCD, or other imaging sensor, with a pixel array or light sensitive regions. As the light is emitted by the light source, the sensor may detect reflected light on one or more pixels, pixel regions, and/or pixel locations.

Based on the reflected light detected by the range of pixels in the pixel array of the sensor, the controller may determine an associated light intensity pattern for the pixel array of the sensor (step 1016). This light intensity may correspond to the calibration reference value used to determine plasma protein levels from whole blood, as described herein. The method 1000 may continue by selecting light intensities corresponding to one or more pixel locations as the calibra-tion reference values to be used in future measurements (step 1020).

FIG. 11 is a flow diagram of a method 1100 for deter-mining a protein level of whole blood obtained from a donor 102 while the donor 102 is connected to an apheresis system 100 in accordance with embodiments of the present disclo-sure. The method 1100 may correspond to step 928 described in conjunction with FIG. 9. A general order for the steps of the method 1100 is shown in FIG. 11. Generally, the method 1100 begins at step 1104 and ends at step 1124. The method 1100 can include more or fewer steps or can arrange the order of the steps differently than those shown in FIG. 11. The method 1100 can be, at least partially, executed as a set of computer-executable instructions executed by a computer system, controller, processor, centrifuge micro-controller, and/or another device and encoded or stored on a computer readable medium. In other configurations, the method 1100 may be executed, at least partially, by a series of components, circuits, gates, etc. created in a hardware device, such as a System on Chip (SOC), Application Specific Integrated Circuit (ASIC), and/or a Field Program-mable Gate Array (FPGA). Hereinafter, the method 1100 shall be explained with reference to the systems, devices, valves, pumps, sensors, components, circuits, modules, soft-ware, data structures, signaling processes, models, environ-ments, apheresis systems, methods, etc. described in con-junction with FIGS. 1-10.

The method 1100 may begin when emitted light (e.g., from the light source) is reflected from the prism sensing surface while whole blood is in the integrated cuvette and prism 124 and the reflected light is received at the sensor of the refractometer 260 (step 1104). As the light is emitted by the light source (e.g., at 420 nm), the sensor may detect reflected light on one or more pixels, pixel regions, and/or pixel locations.

Based on the reflected light (e.g., from the prism sensing surface while whole blood is in the integrated cuvette and prism) that is detected by the pixel array of the sensor, the method 1100 may proceed by determining an associated light intensity pattern across the pixel array of the sensor (step 1108). The light intensity pattern may correspond to a measured intensity of light at each row and/or column of pixels in the pixel array. In some examples, the light intensity may be associated with regions of the sensor.

Using the calibration reference value or light intensity associated with the anticoagulant, the method 1100 may continue by determining a pixel location of the sensor where light is detected (by the sensor) at a predetermined light intensity chosen from the anticoagulant calibration reference pixel pattern (step 1112). This pixel location may be referred to herein as a shifted pixel position. Method 1100 uses the magnitude of the pixel position shift from calibration solu-tion to whole blood to determine protein content of plasma.

The method 1100 may continue by determining whether the shifted pixel position relative to calibration pixel posi-tion corresponds to a pixel shift that is within predetermined limits (e.g., a lower limit pixel shift and an upper limit pixel shift) for plasma donation eligibility (step 1116). In some examples, the lower limit of pixel shift may be associated with plasma having a protein level at 6.0 g/dL. The upper limit may be associated with an upper pixel shift. This upper limit may correspond to a plasma protein level at 9.0 g/dL. When the pixel shift is determined to be between, and/or including, these predetermined limits, the plasma protein level of the whole blood is sufficient for plasma donation.

When the pixel shift is within the predetermined limits, the method 1100 may proceed by sending a "Start Aphere-sis" instruction to one or more components of the apheresis system 100 that starts the apheresis procedure (step 1120). In one example, the command may cause the apheresis system 100 to draw whole blood from the donor 102 and separate plasma from the whole blood for collection. This process may not require any further setup between the donor 102 and the apheresis system 100.

In the event that the pixel shift is outside of the prede-termined limits, the method 1100 may proceed by sending an "Alarm" to one or more components of the apheresis system 100 that prevents the apheresis procedure from beginning (step 1124). The alarm may cause an audible alert to be emitted from a speaker, a visual message to be rendered to a display device associated with the apheresis system 100, and/or combinations thereof. When the pixel shift is outside of the predetermined limits, the donor 102 is disconnected from the disposable tubing set 120 and the entire disposable tubing set 120 including the integrated cuvette and prism 124 is discarded or disposed of.

The present disclosure thus determines plasma protein content of whole blood by measuring reflected light instead of measuring refracted light. Measuring reflected light has numerous advantages over measuring refracted light. For example, when refracted light enters whole blood, the refracted light is quickly attenuated both by RBC light scatter and by RBC light absorption. Refracted light is therefore very difficult to measure. Measuring reflected light is not attenuated by either RBC light scatter or RBC light absorption.

Figure 12A:
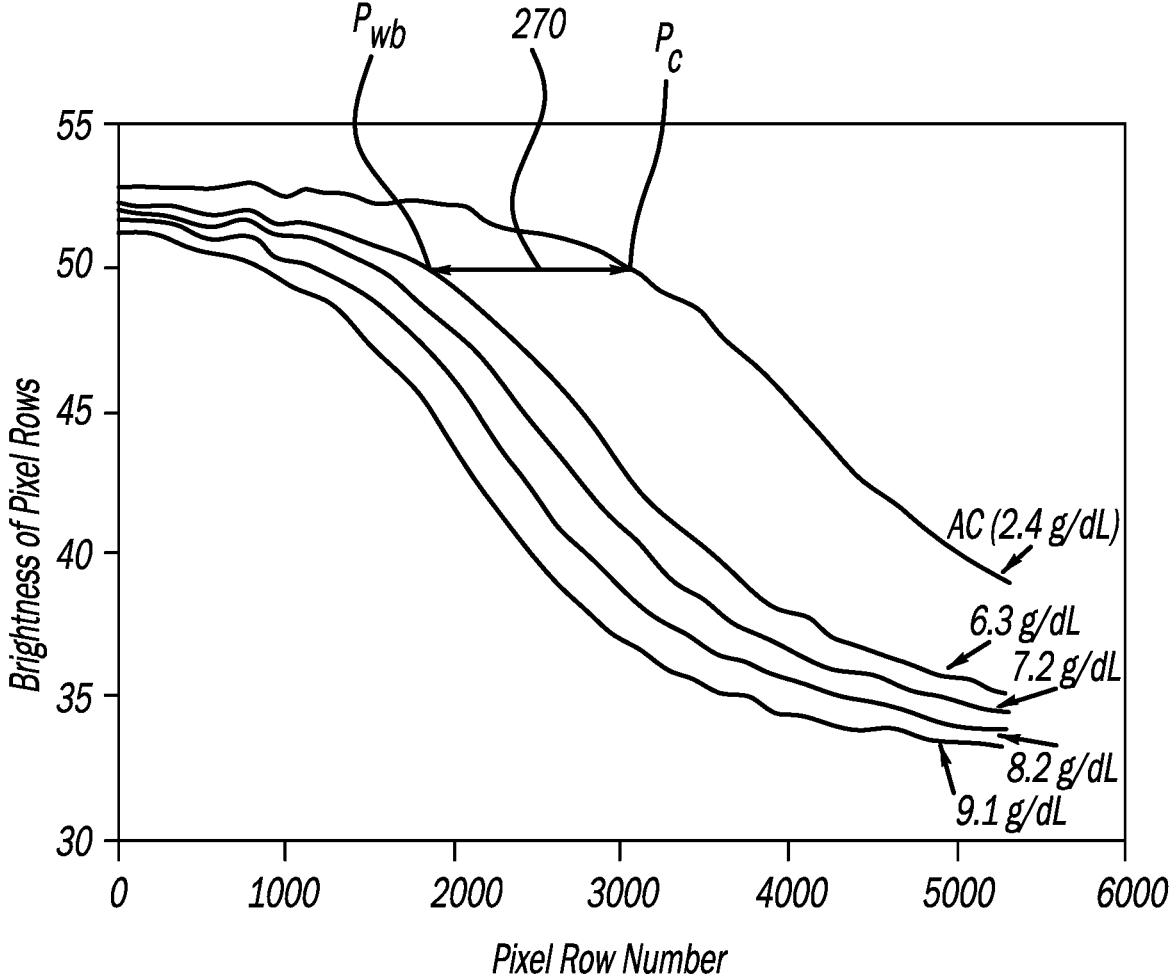
FIG. 12A shows a graph of sensor readings with various density calibration liquids highlighting the anticoagulant calibration pixel pattern in accordance with examples of the present disclosure.

FIG. 12A shows pixel patterns from sensor (e.g., CCD) readings with various density liquids (simulating whole blood with varying (6.3 to 9.1 g/dL) plasma protein content). Also shown is the anticoagulant calibration pixel pattern (AC calibration pixel pattern at 2.4 g/dL) in accordance with examples of the present disclosure. The anticoagulant (AC) pixel pattern simulates the pixel pattern of plasma with a protein content of 2.4 g/dL. Once the AC calibration pixel pattern is established for a specific plasma collection pro-cedure, one (or more) pixel row(s) (Pc) is (are) chosen, and the pixel intensity (Ic) of that pixel row is noted. As an example, in FIG. 12B, the value chosen is 90% of the maximum intensity detected. Whole blood (with plasma protein content of 6.3 g/dL in this example) is then introduced into the integrated prism cuvette. The pixel location (Pwb) measuring the intensity equivalent to Ic is located. The pixel shift is calculated (Pc-Pwb). This value is represented by the horizontal line 270 in FIG. 12A. The plasma protein content of the whole blood sample is then calculated using the equation K(Pc-Pwb)+2.4. Where K is a proportionality constant unique to the overall configuration of the integrated cuvette and prism system.

FIG. 12B is a flow diagram of steps 1204, 1208, 1212, and 1216 expanding upon the description of FIG. 12A above and step 1112 in FIG. 11. Step 1112 requires that, after a disposable set is assembled onto the refractometer in an apheresis machine, for example, a calibration reference (e.g., a calibration pixel pattern) be established using a solution that simulates a known plasma protein content. For example, if anticoagulant is used as the calibration solution, it is known that the pixel pattern obtained will represent a plasma protein concentration of 2.4 g/dL. After whole blood has entered the integrated cuvette in the disposable set, a second pixel pattern representing the plasma protein content of the whole blood is obtained.

At step 1204, from the pixel array pattern established using the calibration solution (Step 1020), a pixel row (Pc) is selected with a brightness (e.g., light intensity) value (1c) of 90%, for example, of the maximum brightness. At step 1208, from the pixel array pattern established using Step 1108 (pixel pattern from the whole blood sample received into the integrated cuvette), the pixel row (Pwb) displaying a brightness (e.g., light intensity) equal to 1c from Step 1204 is identified.

At step 1212, the pixel shift between Pc and Pwb (e.g., Pixel shift=Pc-Pwb) is determined. At step 1216, the protein density of the whole blood plasma using the formula K(Pc-Pwb)+C is calculated. K is an experimentally determined proportionality constant embedded in the software with units of g/dL/pixel. K is specific to the optical geometry, prism material, wavelength of source light, and light sensor (e.g., CCD) resolution. Pc-Pwb is the pixel shift value with units of pixels. C is the simulated plasma protein concentration value of the calibration solution with units of g/dL. In the case of anticoagulant as a calibration solution, C=2.4 g/dL. Although step 1204 describes choosing a single brightness (e.g., light intensity) value (Ic) of 90%, it should be noted that several values of Ic might be chosen, and the pixel shift analysis described in steps 1212 and 1216 might be performed on each of the intensity values chosen. An average of values obtained (step 1216) might then be used to determine the plasma protein concentration. Methods for determining the proportionality constant, K, will be described later in this disclosure.

FIG. 12A shows a graph of sensor (e.g., CCD) readings with various density liquids (simulating whole blood with varying (6.3 to 9.1 g/dL) plasma protein content). Also shown is the anticoagulant calibration pixel pattern (AC calibration pixel pattern at 2.4 g/dL) in accordance with examples of the present disclosure. The anticoagulant (AC) pixel pattern simulates the pixel pattern of plasma with a protein content of 2.4 g/dL. Once the AC calibration pixel pattern is established for a specific plasma collection procedure, one (or more) pixel row(s) (Pc) is (are) chosen, and the pixel intensity (Ic) of that pixel row is noted. As an example, in FIG. 12A, the value chosen is 90% of the maximum intensity detected. Any other suitable intensity value other than 90% may be used, such as 80% intensity, 85% intensity, etc. Also, multiple intensity values may be measured and then averaged. Whole blood (with plasma protein content of 6.3 g/dL in this example) is then flowed into the integrated prism cuvette. The pixel location (Pwb) measuring the intensity equivalent to Ic is located. The pixel shift is calculated (Pc-Pwb). This value is represented by the horizontal line in FIG. 12A. The plasma protein content of the whole blood sample is then calculated using the equation K(Pc-Pwb)+2.4. Where K is a proportionality constant unique to the overall configuration of the integrated cuvette and prism system.

FIG. 12C is a flow chart describing the steps involved in determining the linear proportionality constant, K. Although Step 1262 in FIG. 12C calls out an intensity value of 90%, other values might be chosen, for example, 80%, 60%, etc. Also, an average of more than one intensity value may be used, such as an average of 90% and 80%.

FIGS. 12D through 12G show a series of pixel patterns that are used to determine the constant, K in accordance with steps 1254, 1258, 1262, 1266, 1270, 1274, and 1278 of FIG. 12C.

At step 1254, a calibration solution that simulates a known plasma protein concentration (Cc) is obtained. Using an integrated cuvette and prism assembled onto the refractometer, calibration solution is inserted into the cuvette. A reference pixel pattern is then generated for the calibration solution. At step 1258, using a second solution that simulates plasma of a known protein concentration (Cs), the calibration solution is flushed out of the cuvette leaving the second solution within the cuvette. A pixel pattern is generated for the second solution.

At 1262, using the reference pixel pattern, a pixel row displaying, for example, 90% of the maximum brightness (e.g., intensity) in the reference pixel pattern, is identified. The row number (Ps) and the brightness (1c) is noted. At step 1266, the pixel pattern of the second solution, the row number (Ps) displaying a brightness equal to 1c is identified. At step 1270, the K value is calculated as follows: K=(Cc-Cs)/(Pc-Ps) with units of g/dL/Pixel. At step 1274, steps 1254-1270 are repeated for several solutions that each simulate plasma of known but different concentrations. At step 1278, the K values obtained from each of the several solutions are averaged, and this this average value is used to determine plasma protein concentrations of unknown values.

Figure 12D:
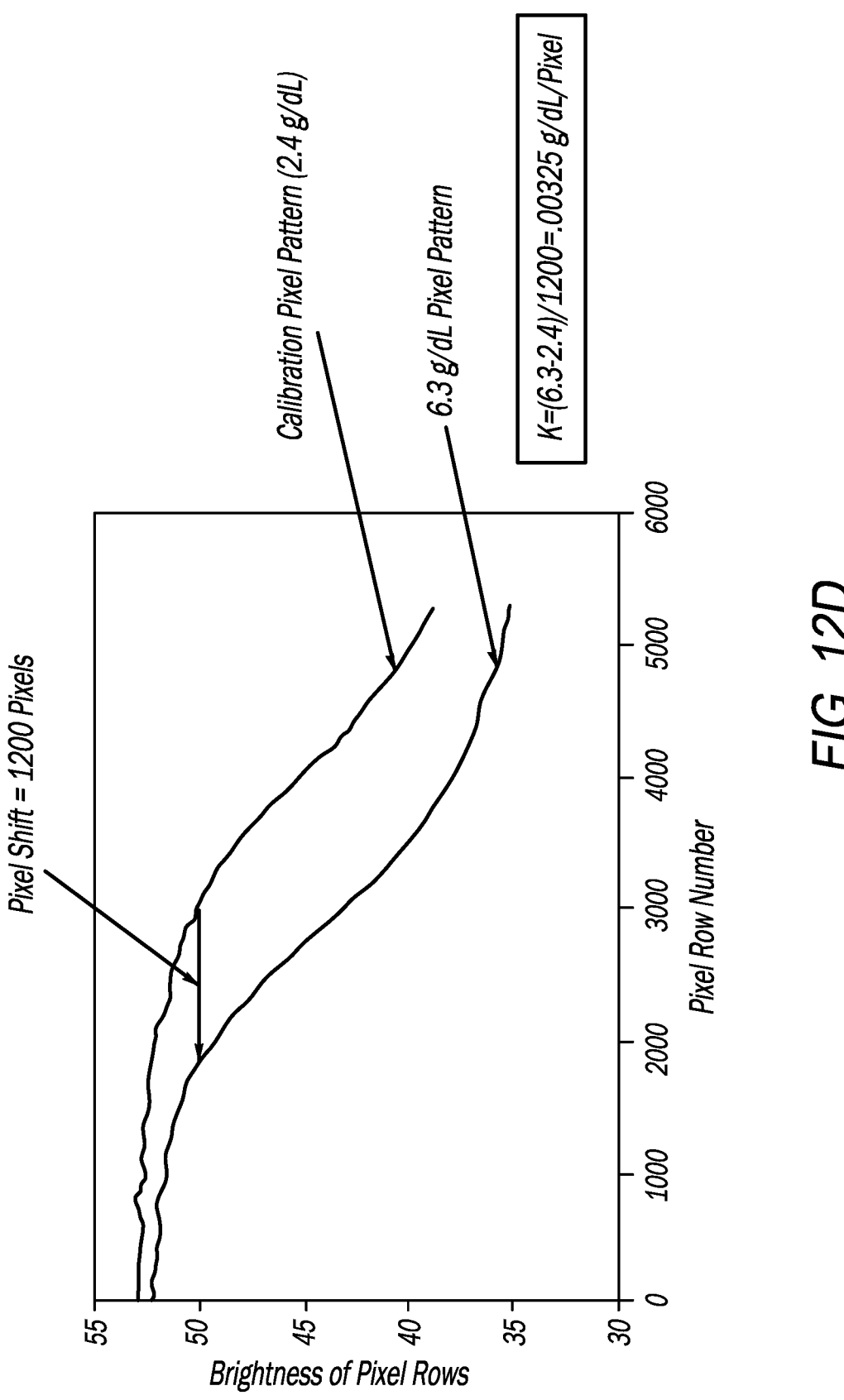
FIG. 12D is a graph of an exemplary first pixel pattern used to determine the proportionality constant K.
Figure 12E:
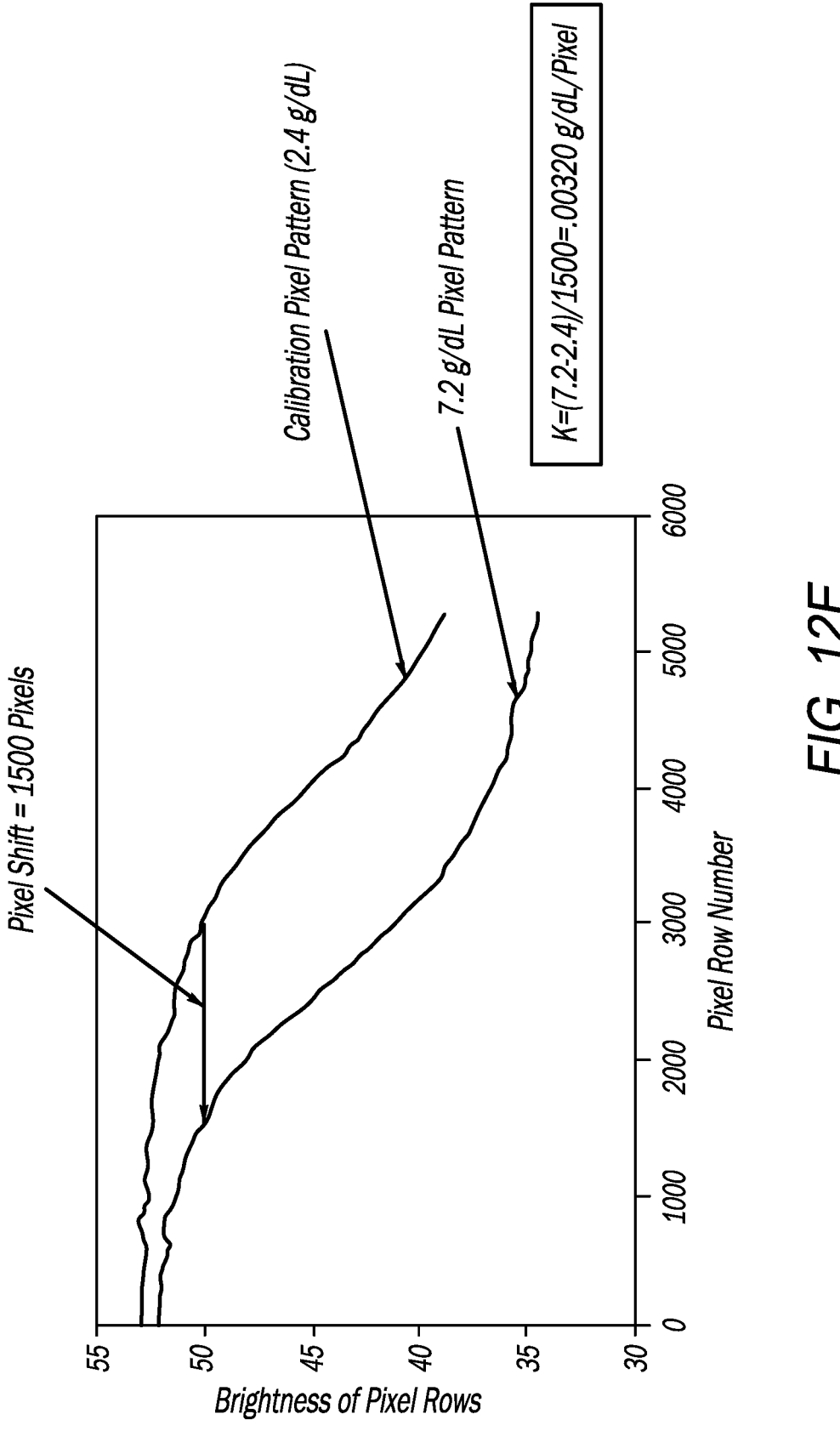
FIG. 12E is a graph of an exemplary second pixel pattern used to determine the proportionality constant K.
Figure 12F:
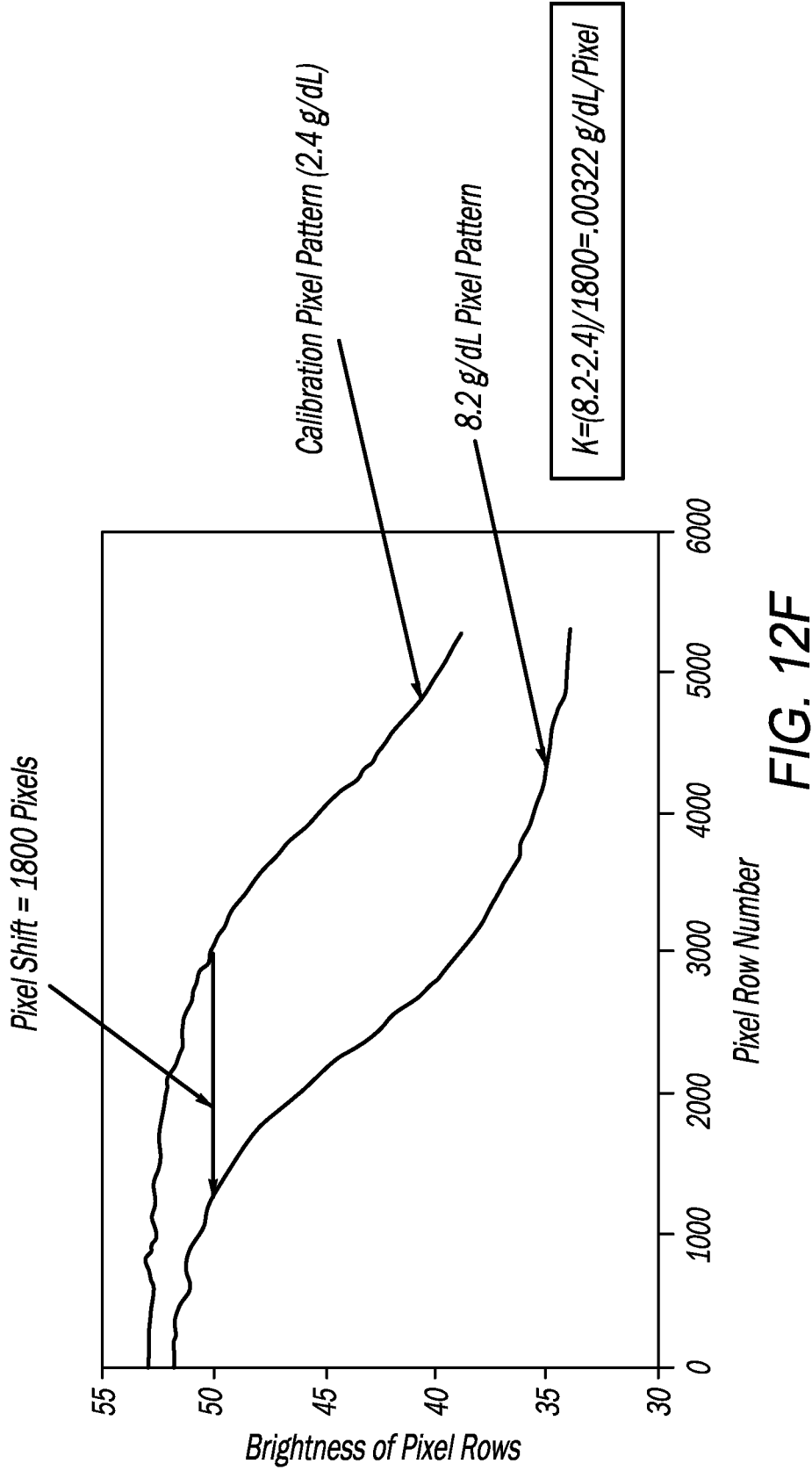
FIG. 12F is a graph of an exemplary third pixel pattern used to determine the proportionality constant K.
Figure 12G:
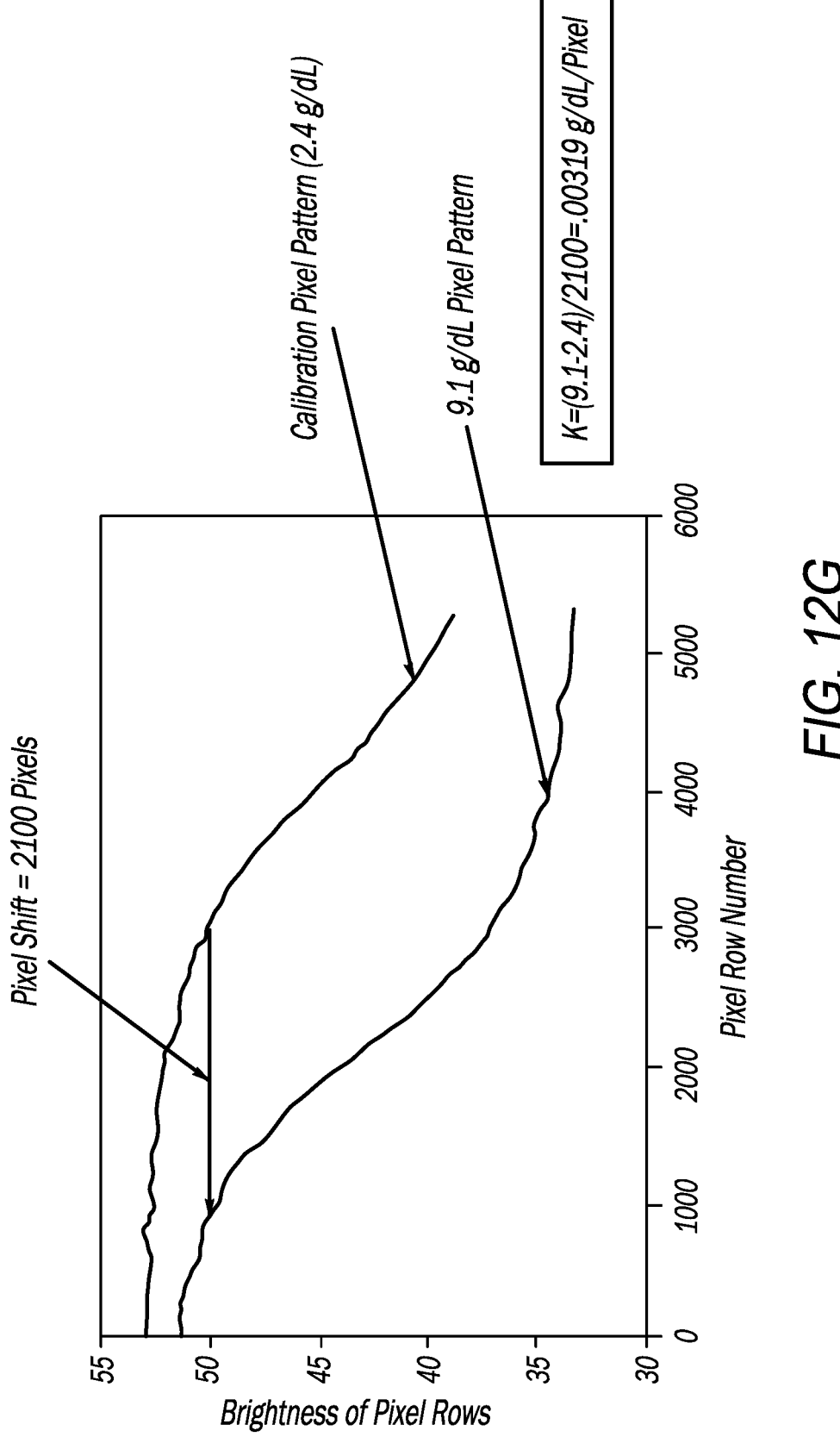
FIG. 12G. is a graph of an exemplary fourth pixel pattern used to determine the proportionality constant K.

In the examples shown, anticoagulant solution simulating a plasma protein concentration of 2.4 g/dL was used to generate the reference calibration pixel patterns. Other solutions simulating known plasma protein content might also be used, for example, a normal saline solution might be used. In addition to the calibration pixel pattern, FIG. 12D shows a second pixel pattern of solution simulating a plasma protein content of 6.3 g/dL. Pixel shift associated with a brightness of 50 is chosen and indicated by the horizontal arrow connecting the two patterns. Note that the pixel shift (from the calibration pixel pattern) associated with second pixel pattern is equal to 1200 pixels (3000-1800=1200). From the information contained in FIG. 12D, the proportionality constant K can be calculated as (6.3-2.4)/1200=. 00325 g/dL/pixel. FIGS. 12E through 12G show repeated calculations of constant K with each using solutions simulating different plasma protein concentrations.

Figure 13A:
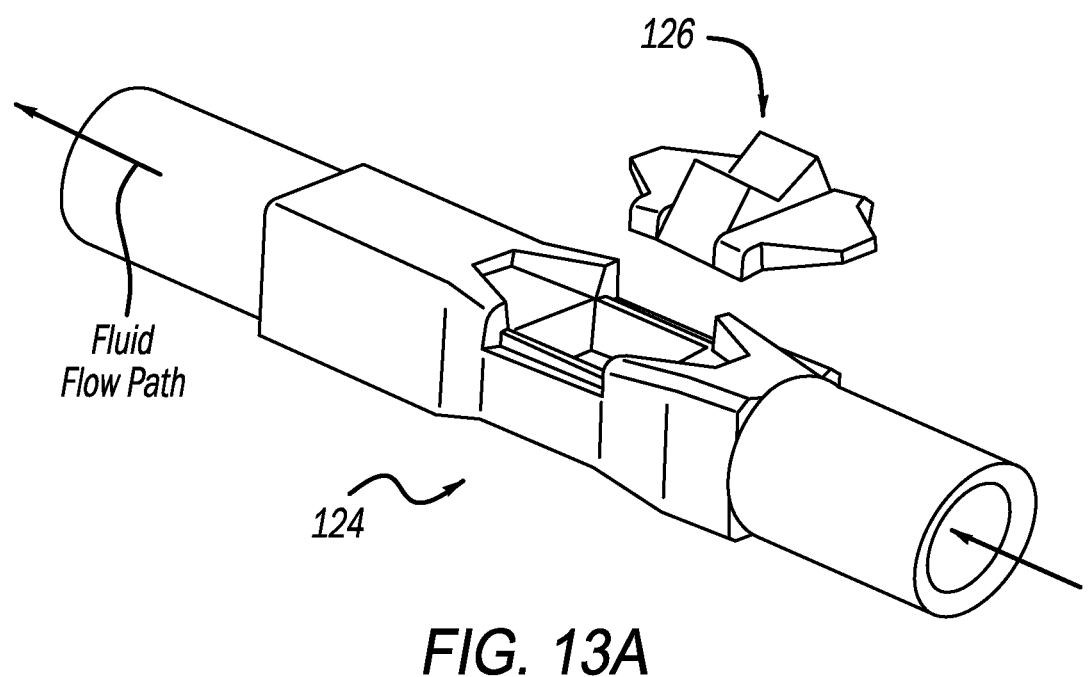
FIG. 13A is an exploded perspective view of an integrated cuvette and prism of the disposable tubing set in accordance with embodiments of the present disclosure.
Figure 13B:
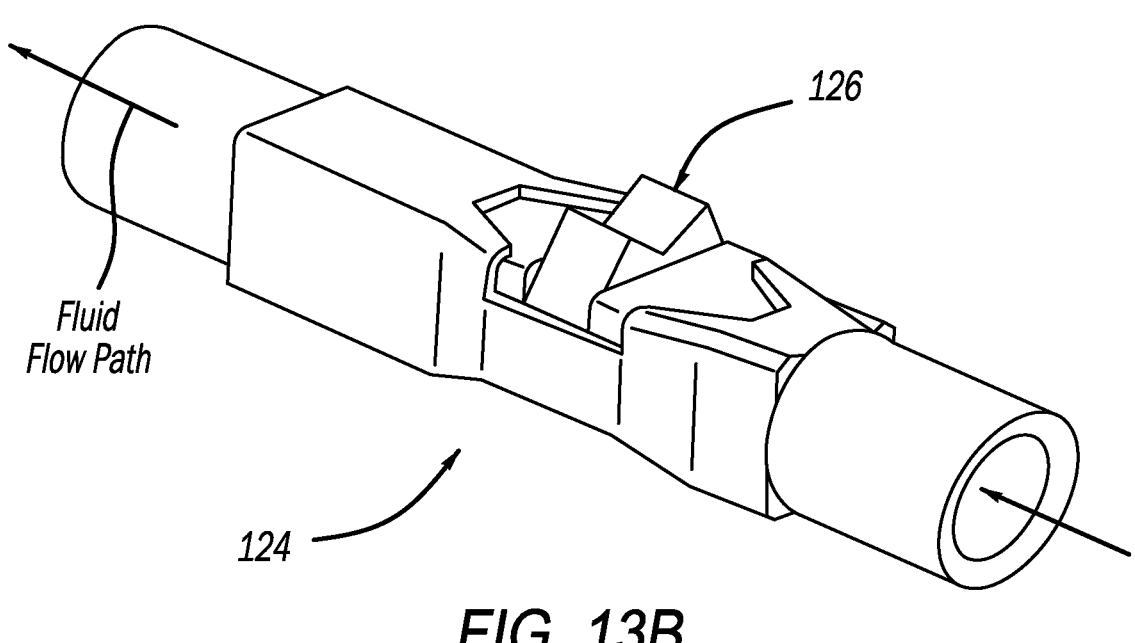
FIG. 13B is a perspective view of an integrated cuvette and prism of the disposable tubing set in accordance with embodiments of the present disclosure.

FIG. 13A is a perspective view of an integrated cuvette and prism substrate (124 and FIG. 4) of the disposable tubing set 120 in accordance with embodiments of the present disclosure. FIG. 13B shows a view of the prism substrate assembled to the cuvette 124 shown in FIG. 13A. The prism is secured to the cuvette 124 in any suitable manner, such as with any suitable adhesive. The prism and the cuvette 124 may also be configured such that the prism mechanically interlocks with the cuvette 134.

Figure 14A:
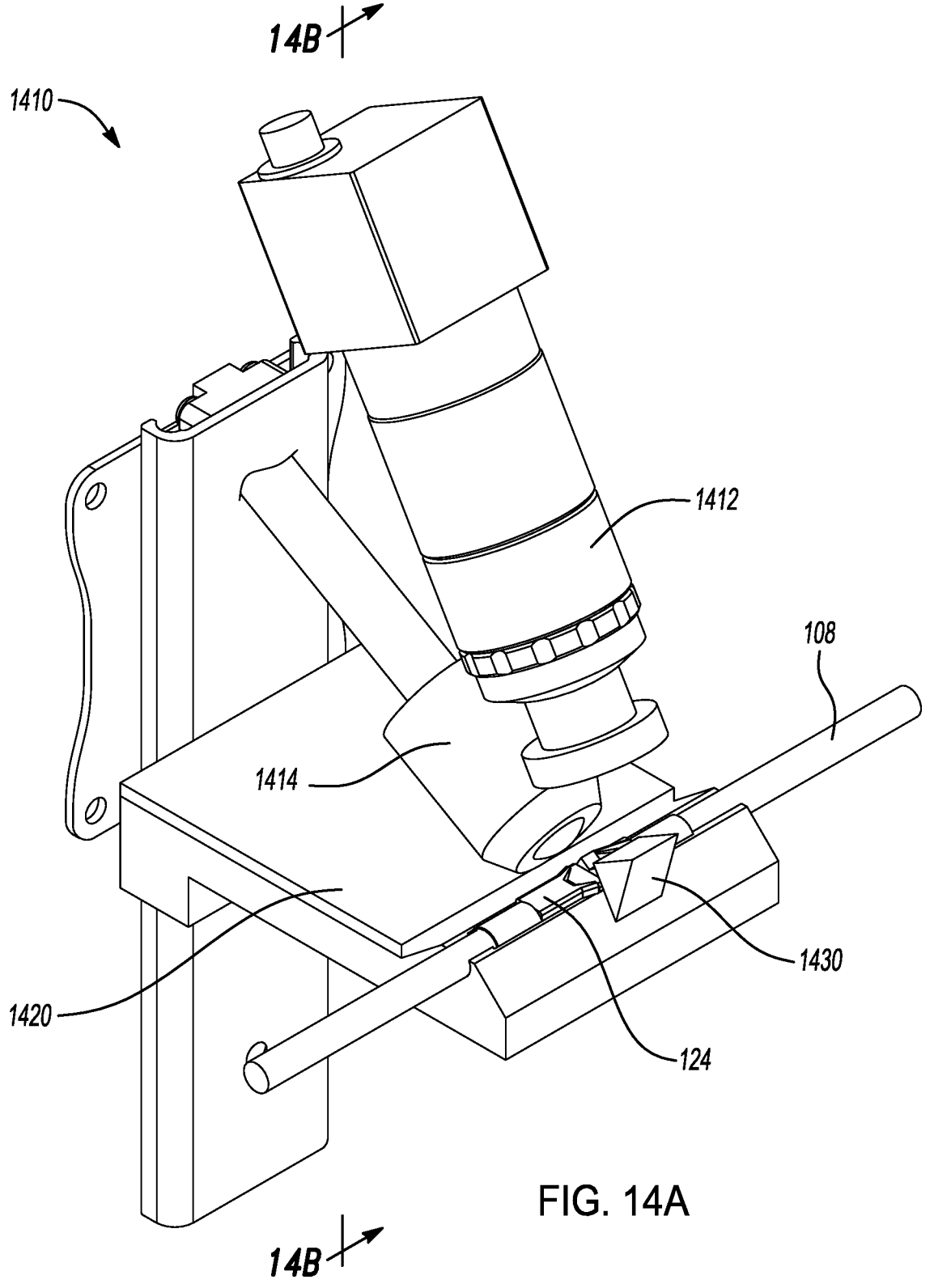
FIG. 14A is a perspective view of an additional exemplary refractometer in accordance with the present disclosure.
Figure 14B:
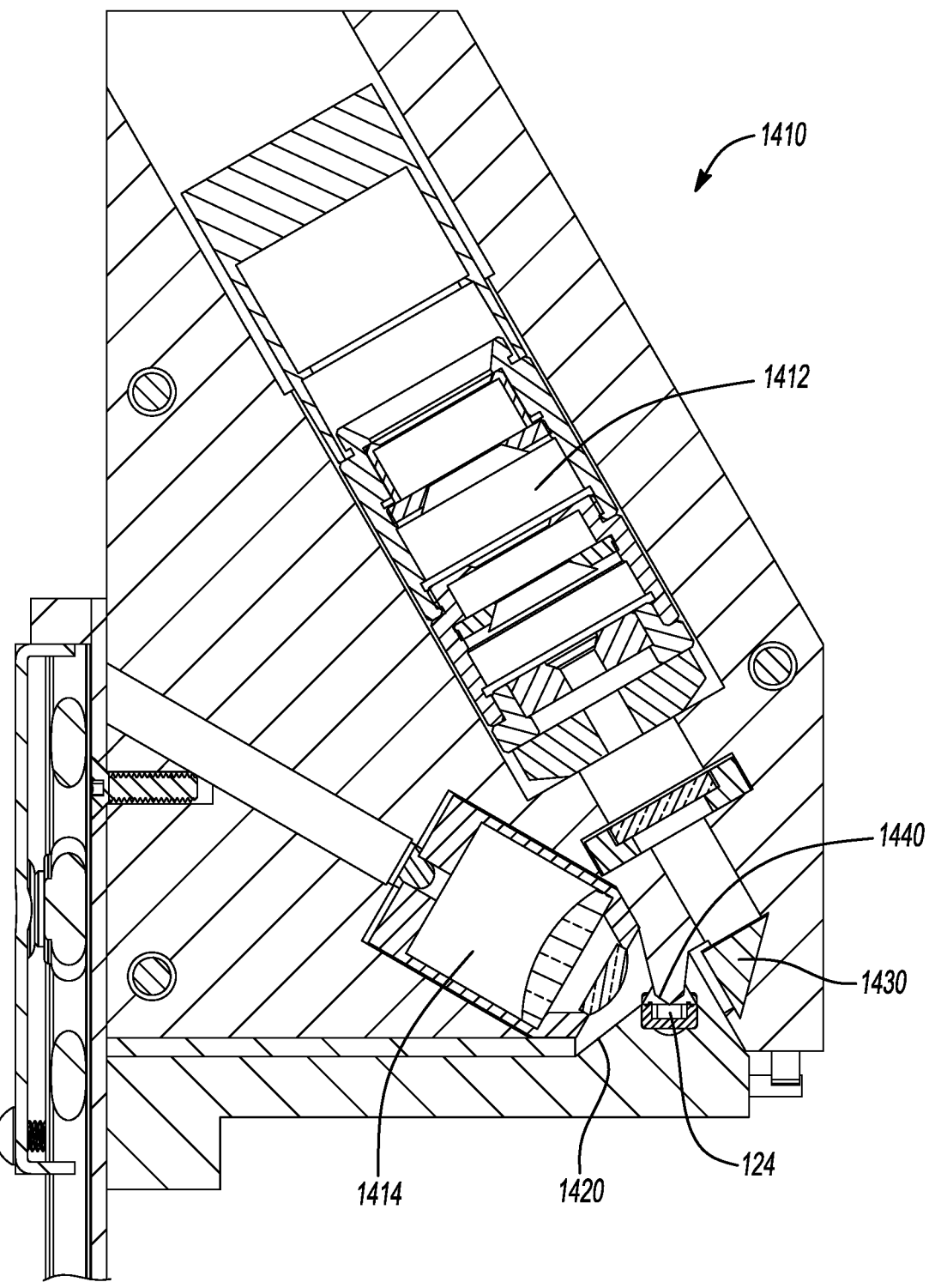
FIG. 14B is a cross-sectional view of the refractometer of FIG. 14A taken along line 14B-14B.

FIGS. 14A and 14B illustrate an exemplary refractometer 1410 in accordance with the present disclosure, and show the interface with the disposable cuvette and prism 124. The refractometer 1410 includes a light source 1412 and a camera 1414. The description of the light source and camera of the refractometer 260 set forth above also applies to the light source 1412 and the camera 1414.

The cuvette (with associated tubing) may be loaded into a tray 1420 and then elevated into position under the refractometer. The prism is positioned above the flow path, which advantageously allows gravity to pull cells away from the sensing surface so a pure plasma layer can be measured without previously removing the cells. A permanent 90-degree prism 1430 turns the reflected light path toward the CCD/camera 1414, which is positioned roughly parallel to the light source 1412. This allows for a more ergonomic layout, so the optical components are not interfering with the operator's motions. A location feature 1440 facilitates precise and consistent location of the cuvette and prism within the apparatus.

The pixel shift method of the present disclosure advantageously improves accuracy of measuring plasma protein content. For example, using the pixel shift method renders irrelevant any potential inconsistencies with respect to loading the cuvette in the refractometer. Further, the present disclosure permits disposable cuvettes to be used because the pixel shift method accounts for differences in dimensions that may be present between various different disposable cuvettes.

This present disclosure thus provides for a method to measure plasma protein content through a disposable cuvette. Integration of the prism and cuvette into a disposable allows for the protein measurement to be taken without an open blood event and the associated risk of infection or contamination. Also, the approach allows for repeated measurement throughout the apheresis procedure if desired.

Disadvantages of the disposable cuvette and prism are that expensive optical components such as glass prisms need to be converted to manufacturable designs and inexpensive designs so plastic components will likely be employed. Also, the disposable becomes part of the optical pathway of the device, which would normally require accurate alignment so that readings between different individual cuvettes and loading events can be accommodated.

This invention addresses these disadvantages by using a calibration fluid (the anticoagulant) and the pixel shift approach. Once the disposable cuvette is loaded into the sensor and the AC fluid is present, a pixel pattern will emerge on the CCD from the reflected light. However, that pattern will have slight position error run-to-run due to small deviations in the loading position of the cuvette or small differences in optical clarity between different prisms. These differences would normally result in measure error.

The pixel shift method is robust to those errors by using only the shift in pattern (rather than the absolute position) between the calibration fluid pixel pattern and that of the blood needing measurement. By measuring the amount of pixel shift only, the device is robust to the specific positions of the pixel pattern.

The present teachings generally measure plasma protein content based on a linear correlation between protein concentration and a transverse pixel shift of refractometer pixel patterns generated by an anticoagulant calibration solution and a sample of whole blood. Further, teachings herein relate to use of a light spectrum (420 nm), which reduces error associated with refracted light being reflected by red blood cells onto the refractometer light sensor.

Any of the steps, functions, and operations discussed herein can be performed continuously and automatically.

While the flowcharts have been discussed and illustrated in relation to a particular sequence of events, it should be appreciated that changes, additions, and omissions to this sequence can occur without materially affecting the operation of the disclosed embodiments, configuration, and aspects.

The exemplary systems and methods of this disclosure have been described in relation to refractometry in apheresis systems. However, to avoid unnecessarily obscuring the present disclosure, the preceding description omits a number of known structures and devices. This omission is not to be construed as a limitation of the scope of the claimed disclosure. Specific details are set forth to provide an understanding of the present disclosure. It should, however, be appreciated that the present disclosure may be practiced in a variety of ways beyond the specific detail set forth herein.

A number of variations and modifications of the disclosure can be used. It would be possible to provide for some features of the disclosure without providing others.

References in the specification to "one embodiment." "an embodiment," "an example embodiment." "some embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in conjunction with one embodiment, it is submitted that the description of such feature, structure, or characteristic may apply to any other embodiment unless so stated and/or except as will be readily apparent to one skilled in the art from the description. The present disclosure, in various embodiments, configurations, and aspects, includes components, methods, processes, systems and/or apparatus substantially as depicted and described herein, including various embodiments, subcombinations, and subsets thereof. Those of skill in the art will understand how to make and use the systems and methods disclosed herein after understanding the present disclosure. The present disclosure, in various embodiments, configurations, and aspects, includes providing devices and processes in the absence of items not depicted and/or described herein or in various embodiments, configurations, or aspects hereof, including in the absence of such items as may have been used in previous devices or processes. e.g., for improving performance, achieving case, and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments, configurations, or aspects for the purpose of streamlining the disclosure. The features of the embodiments, configurations, or aspects of the disclosure may be combined in alternate embodiments, configurations, or aspects other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the disclosure.

Moreover, though the description of the disclosure has included description of one or more embodiments, configurations, or aspects and certain variations and modifications, other variations, combinations, and modifications are within the scope of the disclosure, e.g., as may be within the skill and knowledge of those in the art, after understanding the present disclosure. It is intended to obtain rights, which include alternative embodiments, configurations, or aspects to the extent permitted, including alternate, interchangeable and/or equivalent structures, functions, ranges, or steps to those claimed, whether or not such alternate, interchangeable and/or equivalent structures, functions, ranges, or steps are disclosed herein, and without intending to publicly dedicate any patentable subject matter.

Exemplary aspects are directed to a method comprising: attaching a disposable tubing set comprising an integrated cuvette to an apheresis machine; connecting a plasma donor to the disposable tubing set by puncturing a vein of the plasma donor with a needle in communication with tubing of the disposable tubing set and causing whole blood to flow from the plasma donor into the tubing of the disposable tubing set; connecting an anticoagulant bag comprising anticoagulant to the tubing of the disposable tubing set; pumping the anticoagulant from the anticoagulant bag along the tubing to a space inside integrated cuvette; determining a calibration reference value for a refractometer associated with the apheresis machine based on first light emitted from a light source of the refractometer through a portion of the integrated cuvette onto the anticoagulant inside the integrated cuvette and an amount of the first light emitted that is reflected onto a sensor of the refractometer; pumping whole blood from the plasma donor along the tubing to the space inside the integrated cuvette; activating the refractometer associated with the apheresis machine causing second light to emit from the light source of the refractometer through the portion of the integrated cuvette onto the whole blood inside the integrated cuvette and causing an amount of the second light to be reflected onto the sensor of the refractometer; and determining, based on the calibration reference value and the amount of the second light reflected onto the sensor of the refractometer, a plasma protein level associated with the whole blood in the integrated cuvette.

Any one or more of the above aspects include wherein the method comprises starting, via a processor when the plasma protein level associated with the whole blood in the integrated cuvette is within predetermined limits, an apheresis operation the apheresis machine, wherein the apheresis operation separates plasma from the whole blood. Any one or more of the above aspects include wherein the predetermined limits are no less than 6.0 g/dL and no greater than 9.0 g/dL. Any one or more of the above aspects include wherein the integrated cuvette comprises an integrated prism formed on at least one surface of the integrated cuvette, and wherein the first light and the second light pass through the integrated prism when emitted and reflected. Any one or more of the above aspects include wherein determining the calibration reference value comprises: determining a light intensity pattern of the first light emitted that is reflected onto the sensor of the refractometer; and setting the light intensity pattern measured by the sensor as the calibration reference pixel pattern. Any one or more of the above aspects include wherein determining the plasma protein level associated with the whole blood in the integrated cuvette comprises: determining, via the processor, a whole blood light intensity pixel pattern that is compared to the calibration reference pixel pattern; determining, via the processor, a pixel position shift between a whole blood pixel pattern and the calibration reference pixel pattern where the shift between pixels of the same intensity are measured; and determining, via the processor, whether the pixel shift is within a lower limit pixel shift and an upper limit pixel shift. Any one or more of the above aspects include wherein each shift between the lower limit pixel shift and the upper limit pixel shift corresponds to a known plasma protein level. Any one or more of the above aspects include wherein at least one of the first light and the second light is emitted at 420 nm. Any one or more of the above aspects wherein flow of whole blood is paused to permit gravity sedimentation of red blood cells away from the prism measuring surface. Any one or more of the above aspects include wherein the light source is a light emitting diode. Any one or more of the above aspects include wherein the sensor is a charge-coupled device. Any one or more of the above aspects include wherein the method further comprises: sending, via the processor when the pixel shift is determined to be within the lower limit pixel shift and the upper limit pixel shift, a start apheresis instruction to the apheresis machine causing the apheresis machine to draw whole blood from the plasma donor via the disposable tubing set through the integrated cuvette and separate plasma from the whole blood drawn. Any one or more of the above aspects include wherein the method further comprises: sending, via the processor when the pixel shift is determined to be outside of a range from the lower limit pixel shift to the upper limit pixel shift, an alarm message to at least one speaker and display device of the apheresis machine; and preventing, via the processor, the apheresis machine from starting an apheresis process.

Exemplary aspects are directed to a disposable tubing set, comprising: a tubing connector; a donor feed tube connected to the tubing connector at a first end of the donor feed tube; an anticoagulant tube connected to the tubing connector at a first end of the anticoagulant tube; an inlet tube connected to the tubing connector and extending a length from the tubing connector, wherein the inlet tube is in fluid communication with the donor feed tube and the anticoagulant tube via the tubing connector; and an integrated cuvette affixed to the inlet tube, the integrated cuvette comprising: a body; a chamber disposed inside the cuvette and within the body, the chamber in fluid communication with the inlet tube; and an integrated prism formed from the body and protruding in a direction away from the body, wherein an optical path extends from outside of the integrated prism and the integrated cuvette to the chamber.

Any one or more of the above aspects include wherein the disposable tubing set is configured to interconnect with a donor at a second end of the donor feed tube, wherein the disposable tubing set is configured to interconnect with an anticoagulant bag at a second end of the anticoagulant tube.

Exemplary aspects are directed to a method comprising: attaching a disposable tubing set comprising an integrated cuvette to an extracorporeal blood processing machine; fluidly connecting whole blood of a donor to the disposable tubing set; connecting an anticoagulant container comprising anticoagulant to the tubing of the disposable tubing set; pumping the anticoagulant from the anticoagulant container along the tubing to a space inside integrated cuvette; determining a calibration reference value for a refractometer associated with the extracorporeal blood processing machine based on first light emitted from a light source of the refractometer through a portion of the integrated cuvette onto the anticoagulant inside the integrated cuvette and a first pixel pattern of the first light emitted that is reflected onto a sensor of the refractometer; pumping whole blood from the donor along the tubing to the space inside the integrated cuvette; activating the refractometer associated with the extracorporeal blood processing machine causing second light to emit from the light source of the refractometer through the portion of the integrated cuvette onto the whole blood inside the integrated cuvette and causing a portion of the second light to be reflected at a second pixel pattern onto the sensor of the refractometer; and determining, based on the calibration reference value and the second pixel pattern, a plasma protein level associated with the whole blood in the integrated cuvette.

Any one or more of the above aspects include wherein the calibration reference value corresponds to an anticoagulant calibration pixel pattern. Any one or more of the above aspects include wherein determining the plasma protein level associated with the whole blood in the integrated cuvette comprises determining a pixel shift between the anticoagulant calibration pixel pattern and pixel patterns of known protein level fluids.

Exemplary aspects are directed to a method, comprising: attaching a disposable tubing set comprising an integrated cuvette to an extracorporeal blood processing machine; fluidly connecting whole blood of a donor to the disposable tubing set; connecting an anticoagulant container comprising anticoagulant to the tubing of the disposable tubing set; pumping the anticoagulant from the anticoagulant container along the tubing to a space inside integrated cuvette; activating a refractometer associated with the extracorporeal blood processing machine that emits first light from a light source of the refractometer through a portion of the integrated cuvette onto the anticoagulant inside the integrated cuvette; determining an anticoagulant calibration pixel pattern for the anticoagulant corresponding to reflection of the first light from the anticoagulant; conveying whole blood from the donor along the tubing to the space inside the integrated cuvette; activating the refractometer associated with the extracorporeal blood processing machine that emits second light from the light source of the refractometer through the portion of the integrated cuvette onto the whole blood inside the integrated cuvette; determining a plasma protein pixel pattern for the whole blood corresponding to reflection of the second light from the whole blood; and determining, based on the anticoagulant calibration pixel pattern and the plasma protein pixel pattern, a plasma protein level associated with the whole blood in the integrated cuvette.

Any one or more of the above aspects include wherein the anticoagulant calibration pixel pattern corresponds to a pixel pattern of pixel brightness over a pixel row number for a sensor of the refractometer. Any one or more of the above aspects include wherein the sensor receives the reflection of the first light from the anticoagulant and the reflection of the second light from the whole blood. Any one or more of the above aspects/embodiments as substantially disclosed herein.

Any one or more of the aspects/embodiments as substantially disclosed herein optionally in combination with any one or more other aspects/embodiments as substantially disclosed herein.

One or means adapted to perform any one or more of the above aspects/embodiments as substantially disclosed herein.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

As used herein, the singular forms "a," "an," and "the" are intended to include the plural forms as well, unless the context clearly indicates otherwise. It will be further understood that the terms "include," "including." "includes." "comprise." "comprises," and/or "comprising." when used in this specification, specify the presence of stated features, integers, steps, operations, elements, and/or components, but do not preclude the presence or addition of one or more other features, integers, steps, operations, elements, components, and/or groups thereof. The term "and/or" includes any and all combinations of one or more of the associated listed items.

The term "a" or "an" entity refers to one or more of that entity. As such, the terms "a" (or "an"), "one or more." and "at least one" can be used interchangeably herein. It is also to be noted that the terms "comprising." "including." and "having" can be used interchangeably.

The phrases "at least one," "one or more." "or." and "and/or" are open-ended expressions that are both conjunctive and disjunctive in operation. For example, each of the expressions "at least one of A, B and C." "at least one of A, B, or C," "one or more of A, B, and C." "one or more of A, B, or C," and "A, B, and/or C" means A alone, B alone, C alone, A and B together, A and C together, B and C together, or A, B, and C together. When each one of A, B, and C in the above expressions refers to an element, such as X, Y, and Z, or a class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

The terms "determine," "calculate," "compute," and variations thereof, as used herein, are used interchangeably and include any type of methodology, process, mathematical operation, or technique.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and this disclosure.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

What is claimed is:

1. A method for determining component content of a fluid sample using a refractometer including a light source and a light sensor, the method comprising:

calibrating the refractometer by identifying a calibration pixel pattern of first pixels of the light sensor illuminated by light from the light source that has reflected off a sensing surface of a container including a reference fluid having a known reference density;

identifying a sample pixel pattern of second pixels of the light sensor illuminated by light from the light source that has reflected off the sensing surface when the fluid sample is present in the container;

identifying a pixel shift distance along the light sensor from the calibration pixel pattern to the sample pixel pattern, the pixel shift distance measured between the first pixels and the second pixels having a common brightness; and determining the component content of the fluid sample based on the pixel shift distance multiplied by K, the product of which is added to C, wherein:

K is an experimentally derived proportionality constant specific to at least one of prism material of the refractometer, wavelength of the light source, resolution of the light sensor, and an optical geometry of the refractometer; and C is a simulated plasma protein concentration value of the reference fluid.

2. The method of claim 1, wherein the container includes a prism including the sensing surface.

3. The method of claim 2, wherein the refractometer and the prism are on an upper side of the container such that gravity draws red blood cells of the fluid sample away from the sensing surface.

4. The method of claim 1, further comprising pausing flow of the fluid sample through the container during the identifying of the sample pixel pattern to allow gravity to draw red blood cells of the fluid sample away from the sensing surface of the container.

5. The method of claim 1, wherein the reference fluid includes at least one of an anticoagulant and saline.

6. The method of claim 1, wherein the container is a cuvette including an integrated prism, the sensing surface is at the integrated prism.

7. The method of claim 1, wherein the container is connected to an apheresis machine;

wherein the method further comprises activating the apheresis machine to separate a fluid component from the fluid sample when the component content that is determined is within a predetermined range.

8. The method of claim 1, wherein the fluid sample is a blood sample.

9. The method of claim 1, wherein the component content is a plasma protein content, an anticoagulant content, a saline content, or a liquid content.

10. A system for measuring component content of a fluid sample, the system comprising:

a light source;

a light sensor;

a container including a prism having a sensing surface;

a support member configured to hold the container relative to the light source and the light sensor such that light generated by the light source reflects off the sensing surface to the light sensor;

a controller configured to:

calibrate the system by identifying a calibration pixel pattern of first pixels of the light sensor illuminated by light from the light source that has reflected off the sensing surface when a reference fluid is present in the container supported by the support member, the reference fluid having a known reference density;

identify a sample pixel pattern of second pixels of the light sensor illuminated by light from the light source that has reflected off the sensing surface when the fluid sample is present in the container;

identify a pixel shift distance along the light sensor from the calibration pixel pattern to the sample pixel pattern, the pixel shift distance measured between the first pixels and the second pixels having a common brightness; and determine the component content of the fluid sample based on the pixel shift distance multiplied by K, the product of which is added to C, wherein:

K is an experimentally derived proportionality constant specific to at least one of prism material of the prism, wavelength of the light source, resolution of the light sensor, and an optical geometry of the prism; and C is a simulated plasma protein concentration value of the reference fluid.

11. The system of claim 10, wherein the light source, the light sensor, and the prism are on an upper side of the container such that gravity draws red blood cells of the fluid sample away from the sensing surface.

12. The system of claim 10, wherein the reference fluid includes at least one of an anticoagulant and saline.

13. The system of claim 10, further comprising an apheresis machine;

wherein the controller is configured to activate the apheresis machine to separate a fluid component from the fluid sample when the component content that is determined is within a predetermined range.

14. The system of claim 10, wherein the light from the light source has a wavelength in a range of 370 nm-470 nm.

15. An apheresis system comprising:

an apheresis machine configured to separate a fluid component from a fluid sample;

a refractometer configured to measure component content of the fluid sample, the refractometer including:

a light source;

a light sensor;

a cuvette including a prism with a sensing surface; and a support member configured to hold the cuvette relative to the light source and the light sensor such that light generated by the light source reflects off the sensing surface to the light sensor; and a controller configured to:

calibrate the refractometer by identifying a calibration pixel pattern of first pixels of the light sensor illuminated by light from the light source that has reflected off the sensing surface while a reference fluid is present in the cuvette supported by the support member, the reference fluid having a known reference density;

identify a sample pixel pattern of second pixels of the light sensor illuminated by light from the light source that has reflected off the sensing surface while the fluid sample is present in the cuvette;

identify a pixel shift distance along the light sensor from the calibration pixel pattern to the sample pixel pattern, the pixel shift distance measured between the first pixels and the second pixels having a common brightness;

determine the component content of the fluid sample based on the pixel shift distance multiplied by K, the product of which is added to C; and activate the apheresis machine to separate the fluid component from the fluid sample when the component content that is determined is within a predetermined range, wherein:

K is an experimentally derived proportionality constant specific to at least one of prism material of the refractometer, wavelength of the light source, resolution of the light sensor, and an optical geometry of the refractometer; and C is a simulated plasma protein concentration value of the reference fluid.

16. The apheresis system of claim 15, wherein the light source, the light sensor, and the prism are on an upper side of the cuvette such that gravity draws red blood cells of the fluid sample away from the sensing surface.

17. The apheresis system of claim 15, wherein the controller is configured to pause flow of the fluid sample through the cuvette when identifying the sample pixel pattern.

* * * * *